United States Patent
Frenkel

(10) Patent No.: US 6,503,752 B1
(45) Date of Patent: *Jan. 7, 2003

(54) LYMPHOTROPIC AGENTS AND VECTORS

(75) Inventor: Nitza Frenkel, Tel-Aviv (IL)

(73) Assignee: Ramot University Authority for Applied Research & Industrial Development Ltd., Tel-Aviv (IL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/646,242

(22) PCT Filed: Nov. 9, 1994

(86) PCT No.: PCT/US94/12715

§ 371 (c)(1),
(2), (4) Date: Jul. 23, 1996

(87) PCT Pub. No.: WO95/13081

PCT Pub. Date: May 18, 1995

(30) Foreign Application Priority Data

Nov. 10, 1993 (IL) .................................................. 107557

(51) Int. Cl.$^7$ ........................... C12N 15/63; C07H 21/04
(52) U.S. Cl. ....................... 435/320.1; 435/6; 536/23.1; 536/24.5
(58) Field of Search ...................... 435/6, 172.1, 172.3, 435/69.1, 320.1; 536/23.1, 24.5; 514/44

(56) References Cited

U.S. PATENT DOCUMENTS

| | | |
|---|---|---|
| 5,230,997 | 7/1993 | Frenkel |
| 5,242,820 | 9/1993 | Lo |
| 5,585,479 | * 12/1996 | Hoke et al. ................. 536/24.5 |

FOREIGN PATENT DOCUMENTS

| | | |
|---|---|---|
| EP | 507179 | 10/1992 |

OTHER PUBLICATIONS

Orkin et al Report and Recomendations of the Panel to Assess the NIH Investment in Research on Gene Therapy, Dec. 1995.*

Geng et al., "Identification and Characterization of a Human Herpesvirus 6 Gene Segment That trans Activates Human Immunodeficiency Virus Type I Promoter" J. of Virology vol. 66(3):1564–1570, Mar. 1992.*

Zaki, S. et al., "Isolation of New Virus . . . Disorders," Science, vol. 234, 596–600, 1986.

Schirmer, Eric C. et al., "Differentiation Between Two . . . Herpesvirus 6," Proc. Natl. Scil. USA, vol. 88, 5922–5926, 1991.

Frenkel, Niza et al., "Cellular and Growth–Factor . . . Cultures," Plenum Publishing Corp., 1–8, 1990.

Kondo, Kazuhiro et al., "Latent Human Herpesvirus . . . Monocytes/Macrophages," Journal of General Virology, 72, 1401–1408, 1991.

Lusso, Paolo et al., "Productive Dual Infection . . . HHV–6," Nature, vol. 337, 370–373, 1989.

Frenkel, Niza et al., "Isolation of a New Herpesvirus . . . T Cells," Proc. Natl. Acad. Sci. USA, vol. 87, 748–752, 1990.

Wyatt, Linda S. et al., "Human Herpesvirus 7: Antigenic Properties . . . Adults," Journal of Virology, vol. 65, No. 11, 6260–6265, 1991.

Wyatt Linda S. et al., "Human Herpesvirus 7 is a . . . Saliva," Journal of Virology, vol. 66, No. 5, 3206–3209, 1992.

Pellett, Philip E. et al., "Genomic Heterogeneity . . . Isolates," Plenum Press, 9–18, 1990.

Lawrence, G.L. et al., "Human Herpesvirus . . . Cytomegalovirus," Journal of Virology, vol. 64, No. 1, 287–299, 1990.

Lindquester, Gary L. et al., "Properties of the Human Herpesvirus . . . Elements," Virology 182, 102–110, 1991.

Martin, M.E.D. et al., "The Genome of Human Herpesvirus . . . Endonucleases," Journal of General Virology, vol. 72, 157–168, 1991.

Frenkel, Niza et al., "HHV–6 and HHV–7 . . . Lymphocytes," Develop. Biol. Standard, vol. 76, 259–263, 1992.

Lopez, C. et al., "Characteristics of Human Herpesvirus–6," The Journal of Infectious Diseases, vol. 157, No. 6, 1271–1273, 1988.

Di Luca, Dario et al., "The Replication of Viral . . . Cells," Virology 175, 199–210, 1990.

Cruikshank et al., Lymphocyte Chemoattractant Factor Induces CD4–Dependent Intracytoplasmic Signaling in Lymphocytes, 1991, The Journal of Immunology, vol. 146: 2928–2934.

Glinsky, The Blood Group Antigen–Related Glycoepitopes: Key Structural Determinants in Immunogenesis and AIDS Pathogenesis, 1992, Medical Hypotheses, vol. 39: 212–224.

Fung et al., Detection and Purification of a Recombinant Human B Lymphotropic Virus (HHV–6) in the Baculovirus Expression System by Limiting Dilution and DNA Dot–Blot Hybridization, 1987, Journal of Virological Methods, vol. 19: 33–42.

* cited by examiner

*Primary Examiner*—Sean McGarry
(74) *Attorney, Agent, or Firm*—Nath & Associates PLLC; Gary M. Nath; Todd L. Juneau

(57) ABSTRACT

Human herpes virus (HHV) 7 is capable of binding to the CD4 antigen and the HHV-7 or a binding protein derived therefrom is thus useful as a CD4-ligand for various therapeutic applications. HHV-6 or HHV-7 are lymphotropic and are thus useful as lymphotropic vectors for delivering DNA into lymphocytes.

7 Claims, 24 Drawing Sheets

A.  pac-2  (U1102 left terminus)

tel                            GC motif
(taaccc)$_{51}$ atcccccaa CGCGCGCGCG

Tn
acgccgctatgggaggcgccg TGTTTTT 33                    terminus
caccaacacgcgccgctgcgagagacgcgtg B.  Pac-2 / Unique sequence junction tel                            GC motif
(taaccc)$_{51}$ atcccccaa CGCGCGCGCG Tn
acgccgctatgggaggcgccg TGTTTTT 33
caccaacacg cgccgctgcgagagacgcgtg Unique
AAAAAAA ctccccattggttgcggcccgagtcgcccgcg
Cgcggaagacacgcgtgtcgtggatgcgcgagccccccccgcacc
ccccgaaagagcggacgacggtatagggcggacggcgcgtagttta
aaggcgagggtgagcgcgaagaaccgatggcgccggcgagagaaa
gagagagagacgggaggcagagccgcagagggcagacgagg

FIG. 5 atacgccggaggagagagaacggccgcggtcgttcccgaggagggc
ccgcgcgcggcgc

C.       pac 1

| end | terminal repeat C Gn | | 41 | |
|---|---|---|---|---|
| | acctcgcgtt | ttaaaaatta | cgtcaaa | CCCCC |

| | T motif | Gn |
|---|---|---|
| GGGGGGG | ttAAAAAA | GGGGGGG | taata acccTaaccc taaccctaac cctaacccta accctaaccc taaccctaac cctaaccctaac cctaacccta accctaa (CCCTAA)$_n$ . . .

FIG. 5 (cont'd)

het-reverse(HdIII)

| | | | |
|---|---|---|---|
| 1 | TNNGGGGCtT | ACGCCAAGCt | TTAACNCTTT |
| | TTAAACNTAA | CATTTCGGAG | |
| 51 | GTAGAAAATT | TAGAAATGAT | TTCCGATAGC |
| | GTCCGTCCCC | TCGGCGTAGA | |
| 101 | ACTTCNACCT | TCGTAAATGT | TAAAATAAAT |
| | GTCTTTGTCA | TAGTANTTTG | |
| 151 | CGGTATAGCT | ATGTTTATCC | TCTGGAGGCG |
| | GTGTGGATTT | CACGGTTCCC | |
| 201 | GCACGTCGGT | GGGCCGTAGC | GTTCGTTGGG |
| | GCCGTCGCCA | TCGAAAACGC | |
| 251 | GCACAAAAAT | ATCAGCGCAC | AAGGATCTCG |
| | GCGGGTTTCA | TAGCGCTCAG | |
| 301 | CCTTGCGGGT | TGGCATTCTT | CGTCTCAGTC |
| | TTTGTGAAAA | TTTCGTATTG | |
| 351 | CGCGAGACAA | ACAGGACAAG | GAGTAAAGGA |
| | AGATGATGTT | AAATaGATAT | |
| 401 | AGACGAGAAC | AAACGCGAAA | CAGATCCTAT |
| | GACGACGGGA | GAAATAATTA | |
| 451 | ACGGTCGcGT | CGGGGACATC | GcGTGATCAA |
| | AGCATGAAAA | TTATGAATGG | |
| 501 | GNGTGANAAA | TTTTTTTGTT | CCNAAGCGGG |
| | GGTCAANCCG | NCCNTNGATG | |
| 551 | NAAGNGGTCA | ACTCNCTATC | ACCGGGANNC |
| | GNNGGTNTNG | GGGANANGC | |

FIG. 6 a

```
tnggggaatt cgagctcggt acccgggatc
ctctagagtc gacctgcaga aaaacggcag
ctatatggcg ataactgttc cggtccgggt
acggtccggc tgagcggagt ggagatagac
cgcttttatg agaacaagtg acccggccgg
agtgccgttg agtgcctcag aggtgagtag
gagaggccgg agaacgggt aaacgcgcgc
ccggtgcgcg cgttgtgtga taagtctgca
acgggcgcgg tcataaacag acagaggaag
atagcagaat agagagaaag agataaaaag
agaggaaaga attacgcaga cttaatatct
gaccaccaaa acgacagtct acacacacgc
ccggttacgg aaaagatgag cgtcagagta
ctgatcgcca tttggcgatc agatgtattt
tcttcgctat cggnttatac cgctccctct
ccgcttattt tgcgcagctg acatgatcgg
cccgatcact tcgattcgtt gtcgcaagat
acgcgacaac tttcaccagg gtntttgagg
tgaattggca tagtttaag cgnacgnnag
attacnccnn tgnggcatt tnttnggac
tttnntggac catatataat ttttgtgcac
tctctagttg cattaatttg tcatggcttt
tgattcacgc gaatgttccc cgacgcgaac
cgtttaatta ttgtctgcgt cataggatct
gtttcgcgtt tgttctcgtc tatatctatt
taacatcatc ttcctttact ccttgtcctg
```

FIG. 6b

```
tttgtctcgc gcaatagaaa ttttcacaaa
gactgagacg aagaatgcca acccgcaagg
ctgagcgcta tgaaacccgc cgagatcctt
gtgcgctgat atttttgtgc gcgttttcga
tggcgacggc cccaacgaac gctacggccc
accgacgtgc gggaaccgtg aaatccacac
cgcctccaga ggataaacat agctataccg
caaantacta tgacaagac atttatttta
acatttacga aggtngaagt tctacgccga
ggggacggac gctatcggaa atcatttcta
aattttctac ctccgaaatg ttangtttaa
aaagngttaa agcttggcgt aagccccnna
```

FIG 6b(cont'd)

```
gtcgacgcga cacacacaga ggacgggcgg
acgcatctcg gtccggcgca acgaggcgag
actggcccac gcgcgagccc gtgcccgctt
cgactggctg ctcctggccc gcggcaggcc
gtccaaactg tacggctatg cgagccggca
tcgcggagaa ctgatccacc taccgtggcc
gccgtcctgg tgtctagaac tcaccacgat
ccgtacagag acgccagaag tgccaccgtg
tggggccacc gctggggttg ccagcgacgc
acgtgagacc cagatgcgtt caagactgcg
gtgagtaaac gtacgggcga gccgcgggga
gggatgtcgg tcagacagtg agtgagtaca
aggttcgtcg agaaccacca gagacaccag
ccggtagaga gtggggacaa aaaaaaaacg
tcacgtcagg ggccgcagt  aacggaaaac
gagtatgaat acgaggaggc gagacgaaac
atagtcaagt atgtgacgcg ccggatcgta
aggcagtaaa gccgatgacg gcctccggcc
ccagagacga ctcgcggagt ggagtccagt
tattctattt tttttgtgat ttttttatc
cacaatccgg tatccgtgaa tccccgcaga
ggtactttcc attaacgatg gtacaggcgg
tataacttcc ggaacacggt gattacggat
atcctgtctc gtttacgcga gacctctttg
```

FIG 7

```
ttgtaatctc ctataacggt aaaaaaaaac
acaaagaaa  gattacagct cctccttttt
tctgcgttat ggcatcctcg cattagtcac
cattcctgtc gcgtgtgctt ttcgctttga
attgtacgcg acaggatacg aatccgttat
actccacaag ggcatagcga ccacggctgt
atgcggcatc tcccgttcca cggatgcct
ttgcgtgtgc agatgttctg tgctttttt
atacggtcag agaccacaga caaaataag
gcaacgccca ccataacgtt tatggtttct
tgttgttttg tttgcgttaa acgcctcttc
tatcgtgtcg gccggatcca tcatgttcaa
tcgttgacgt acgcgcgtcc catcacagcc
ctagactcct gtctgtacgt atgttgcgga
tacggagaga aacttcaacc cgtgggtttc
gtaaagtcgt atgtaaccaa ctcccagctc
gacacgctcc gcgtcgctcc tggtgggcaa
agacggagcc gtgtacgtcc accacactga
gggcggcaag actctgccga ctggcgtcga
gcacaacgga gtttacaaga cgagggctgc
aacgcgacgc cgtgacgtat gaagaagacc
tagagctgcc ggaccagcgt atgtgcggag
cgaacgtccc gacatctgtt cgacgtgatc
```

FIG 7 (cont'd)

```
gccgcggccg ccgacgaaca caacctgctg
accgtcggcg gcctgtgtca gacgcacgcc
ggagtgtcct gcaacttact agagaccgtg
ggagatccgt ggacggcggt tccggccgcg
cgcatgactc tgaccgtgcc gcaggttcag
taccggttat ggcccgaagc ccggagagac
ctccgccggc acctgtacgc gggccacccc
ctgggaccgt ggctcgtgtg cggcgttctc
tctcgagaga gggagacgca gaagccgtcg
cctccgatac gtacgactgt gggaaacgta
ccaacgccgg ggccacgcga ggtggagatc
gcttgggtgg tcttgacttt ggcgggacct
ctgttagcgt tctggcccga taccggcaag
atctctcgtc tggcaaactc gttttccacc
ttatggaaga tgggaccgcg ggccatgaga
ggacactgca cgtactcggc cccgggtaga
catctcccg gggacgcgtg gccactgtgc
gaacacgtga daccgcaggt gggaagctt
ccgaggaaga gagcgtacct ggattagacg
ccacggaggt gaagtaagca tgtcacctac
ggccagagac gtgaccggag gaaaatcatc
```

FIG 7 (cont'd)

```
catatgtgtg gggtgtgtat gcgtggggtg
cgtatgcgtg cgcgtactcg ttttccttcc
ctcttccctt taacccacg aaaaataaaa
tccacgaacg tagacagtca cacacagggt
gcttacgctc cgtgttactg atggcaggta
accaaaaaaa cgtatctctc ggccgtgatg
caccgccgct ctatagcgta gtcgctatag
cagcgcccga tgccaacgcg acagggtgag
tcacatagat cgggactgct tgaaagcgcg
tcgcgttcgc ttcttatata ggcaccccgg
ggggtgggag gagtgaacat acaaggagg
tgcgtccggg attggaggcg aacgtagaaa
acgaacagcg tcagaaaat ataagaaaag
gcggagacac atagccttgg cgggaagacg
acaacaggtt taaaataga cagtcaaaaa
aatagcagac tgtgacgtcc aatacacatg
tggcgatcat ccaatcaacg gggtgtatcg
aggcgcagag acaaagtat gcggaagtac
acacgacacg gtaacgcgga ccgaagacag
agggcgatcg ctagcatggc aagtgtaaga
aaaaaaaac cacgttccaa aaacacctat
acgggaaaca tctcttcact ccctcccgt
cccaaccacc gcaacattca cctccgtaat
```

FIG 7 (cont'd)

```
ccgttgtcac cgcgtttcta ccacggacgc
gtacacacgc agacacacag acacgcacaa
cccacccatg tggtagtcgc gggtgggtac
gtagatgggg cataccgggg tgagacgtga
agacaattca aaacgacatc gcgcgcgacg
tgccaccgtc tgggaccac ggtcgcctgg
cacggtgcca aaggaaacca ccggctaacc
ctaaccctaa ccctaaccct aaccctaacc
ctaaccctaa ccctaaccct aaccctaacc
ctaaccctaa ccctaaccct aaccctaacc
ctaaccctaa ccctaaccct aaccctaacc
ctaaccctaa ccctaaccct aaccctaacc
ctaaccctaa ccctaaccct aaccctaacc
ctaaccctaa ccctaaccct aaccctaacc
ctaaccctaa ccctaaccct aaccctaacc
ctaaccctaa ccctaaccct aaccctaacc
ctaaccctaa ccctaaccct aaccctaacc
catcccccaa cgcgcgcgcg cacgccgcta
tgggaggcgc cgtgttttc accaacacgc
gcgccgctgc gagagacgcg tgaaaaaaac
tccccattgg ttgcggcccg agtcgccccg
cgcgcggaag acacgcgtgt cgtggatgcg
```

FIG 7 (cont'd)

```
cgagccccccc  cccgcacccc  ccgaaagagc
ggacgacggt  ataggggcgg  acggcgcgta
gtttaaggc   gagggtgagc  gcgaagaacc
gatggcgccg  gcgagagaaa  gagagagaga
gacgggaggc  agagccgcag  agggcacacg
aggatacgcc  ggaggagaga  gaacggccgc
ggtcgttccc  gaggagggcc  cgcgcgcggc
gcgagagagg  gtgtagagcg  gacgcgcgta
gagacgcccc  gccgggcggt  tgacctttcc
gcagacattt  ttgcagaccc  ccgacccgtg
tcactgatgc  aaacacgcgc  gcgaacgtac
acagacacgc  cgacgcgccc  caccgagcag
accgccacgt  gagcgaaaac  acacacgcgc
gcgaaaaaa   aaacacacaa  aaaaatacac
acacgcaaaa  aaatacacac  acgcgaaaaa
aaataattta  tgtatgcatt  gttatcacga
tgttaacata  aaacaacaac  aataacaac
acaataacaa  caaccacagc  agcagcatta
actacatcaa  ctacattaac  agacgaggac
ggaatcaccg  gatgtcgac
```

FIG 7 (cont'd)

```
aagctttatc ccaccggtcc ttcctcaaca
tttacgcgtg gctgtctttg agtcgagggt
ctccgcgaaa agtgtacgga tatgccttca
ggcacacagg agaactcgta gcattgccat
ggccgcctaa ctggagcctg gaacttcacc
acgatccta tcgagacgcc agaccacaaa
ccgtttggag tcaccgctgg ggatggcctg
caacacacgt gacagctcgc acggtgcggg
actgcggtga gtgtaagcag tgtgacacat
tgttatcgca attgtcttac ccgattaact
ttttattaat gtattaagca ctctttcttc
acgtgtgact gttgtgtttt ttgttgttat
ctacatcccg gcagcctcg acacgcatat
gtacgtgtgc tgcggacgcg gagaaagtt
gcagcccgtc ggatacgtac gcaacagagc
cgcgccttca gacctgaact cgttacgcgt
cctcctcata gccaggacg gagcaatgta
tgtgcatcac atgagaacgg cgcgactgtg
ccgcctagcc agcagtgtga ccgaattcgc
gcgacgaggg ctgcagcgag aatccgaggt
ttatgaagat gatgttcct tgccagaccg
tcgagtaggt tcggcaacgg ccattcacct
gtttgacgta attacccagg cagccgatgt
```

FIG 8

```
ccacgaccta ctcaccgtgg ccggactgtg
tcagactcac accggcgtca gctgccaact
gtggtataca gaccacgatc cccacaccgt
cgctggggcg gcacgcttca cactgacggt
cgcacggcag cagtatcgat tgtggccaaa
cgcacgacgc aaactgctgc agcacctaca
tccggaccac ccacttgggc tgtggctgtt
gtgtgccgtg ctcacgtacg atgcaaaaga
gacgaatcgc gcagtccac ccgtaacgcc
aggggccgaa accgtgtggg tgatagttac
tggcaggggt gccattctag gattctggcc
agagagcgcc aaaatgtgca gattggcctc
gtctatgaaa ggactctgga aaaacggagc
ccgggcgcta aaaggtcact ggacatacgc
agcacccggc cggcatagag cgggagaggc
ctggcctttg tgtgcacact accaatctcc
tagatacaac aaaattaaaa agattaaaaa
aaaaagaaa aaaagtacaa gagtgttatc
gcgaaacagc gtgtcaaaaa aaaaaacaat
ccacatactc tagaacaaac tgtacccaaa
ataagtccg tgtgcaaaac tgggaaaaaa
aaaatcacct tcctcgttgc cactagaggg
agtaccgaaa gtgtaggcaa gaaggccacg
```

FIG 8 (cont'd)

ctgtaaatga ctgtcagcgt ttggcgctga
aaacattgct gttcttgctg gctcaagcac
aatcacgtga ttaagattcc tttcgttttc
aaagtgtgcc cgggaggcag acatgccctt
tctcgtgaga cattatgaga tttgcctgcc
agagaaccac gtgacttgga cttactttcg
ttttctaaac gtgcctcta ggcatgaatg
ctctttagcg ttagccatga ggctagcgtg
atcctgtata gtacataagt ttctaagaat
atgtttttaa caataatcat gtcccaaaaa
gtcgcgagtg actaaattc tctgtaaatg
aaggcaaatt aaacaggata cagacagttg
tggcagtggt ccgtttcgtc tttctgtgtt
ttccttacgc ggctgacgag gtaaagtgtc
tcagtccata ttgttgtctg tgccaccgta
gttagcggtg gcatactaaa aactccgata
gatgcagaac aataaccg aaaaccacgc
tgtggaacca gaccacactt tataaacaaa
acggccttat cacctggaaa aaaaaactaa
aaataaggca atgatacacc tgactttcca
ttggaaacct gccgtaaccc tgaccacaaa
tcccatgcta aatccctga aacactgcca
aacgtcgcta caaggttttt ccgggatcga
gccgcagcaa gctt

FIG 8 (cont'd)

SEQUENCE LISTING

<160> NUMBER OF SEQ ID NOS: 7

<210> SEQ ID NO 1
<211> LENGTH: 87
<212> TYPE: DNA
<213> ORGANISM: Human herpes virus-6

<400> SEQUENCE: 1

| taacccatcc cccaacgcgc gcgcgcacgc cgctatggga ggcgccgtgt ttttcaccaa | 60 |
| cacgcgcgcc gctgcgagag acgcgtg | 87 |

<210> SEQ ID NO 2
<211> LENGTH: 366
<212> TYPE: DNA
<213> ORGANISM: Human herpes virus-6

<400> SEQUENCE: 2

| taacccatcc cccaacgcgc gcgcgcacgc cgctatggga ggcggcgtgt ttttcaccaa | 60 |
| cacgcgcgcc gctgcgagag acgcgtgaaa aaaactcccc attggttgcg gcccgagtgc | 120 |
| cccgcgcgcg gaagacacgc gtgtcgtgga tgcgcgagcc cccccccgca cccccgaaa | 180 |
| gagcggacga cggtataggg gcggacggcg cgtagtttaa aggcgagggt gagcgcgaag | 240 |
| aaccgatggc gccggcgaga gaaagagaga gagagacggg aggcagagcc gcagagggca | 300 |
| gacgaggata gcgcggagga gagagaacgg ccgcggtcgt tcccgaggag ggcccgcgcg | 360 |
| cggcgc | 366 |

<210> SEQ ID NO 3
<211> LENGTH: 144
<212> TYPE: DNA
<213> ORGANISM: Human herpes virus-6

<400> SEQUENCE: 3

| acctcgcgtt ttaaaaatta cgtcaaaccc ccggggggt taaaaaggg ggggtaataa | 60 |
| ccctaaccct aaccctaacc ctaaccctaa ccctaaccct aaccctaacc ctaaccctaa | 120 |
| ccctaaccct aaccctaacc ctaa | 144 |

<210> SEQ ID NO 4
<211> LENGTH: 574
<212> TYPE: DNA
<213> ORGANISM: Human herpes virus-6

<400> SEQUENCE: 4

| tggggcttac gccaagcttt aaccttttta actaacattt cggaggtaga aaatttagaa | 60 |
| atgatttccg atagcgtccg tcccctcggc gtagaacttc accttcgtaa atgttaaaat | 120 |
| aaatgtcttt gtcatagtat ttgcggtata gctatgttta tcctctggag gcggtgtgga | 180 |
| tttcacggtt cccgcacgtc ggtgggccgt agcgttcgtt ggggccgtcg ccatcgaaaa | 240 |
| cgcgcacaaa aatatcagcg cacaaggatc tcggcgggtt tcatagcgct cagccttgcg | 300 |
| ggttggcatt cttcgtctca gtctttgtga aaatttcgta ttgcgcgaga caaacaggac | 360 |
| aaggagtaaa ggaagatgat gttaaataga tatagacgag aacaaacgcg aaacagatcc | 420 |
| tatgacgacg ggagaaataa ttaacggtcg cgtcggggac atcgcgtgat caaagcatga | 480 |
| aattatgaat ggggtgaaaa ttttttttgtt ccaagcgggg gtcaaccgcc tgatgaaggg | 540 |
| tcaactccta tacaccggga cggggtgggg aagc | 574 |

<210> SEQ ID NO 5
<211> LENGTH: 1141
<212> TYPE: DNA
<213> ORGANISM: Human herpes virus-6
<220> FEATURE:
<221> NAME/KEY: unsure
<222> LOCATION: (2)..(1140)
<223> OTHER INFORMATION: Human herpes virus-6

<400> SEQUENCE: 5

| | | | | | |
|---|---|---|---|---|---|
| tngggaatt | cgagctcggt | acccgggatc | tctagagtc | gacctgcaga | aaaacggcag | 60 |
| ctatatggcg | ataactgttc | cggtccgggt | acggtccggc | tgagcggagt | ggagatagac | 120 |
| cgcttttatg | agaacaagtg | acccggccgg | agtgccgttg | agtgcctcag | aggtgagtag | 180 |
| gagaggccgg | agaaacgggt | aaacgcgcgc | gccggtgcgc | gcgttgtgtg | ataagtgctg | 240 |
| caacgggcgc | ggtcataaac | agacagagga | agatagcaga | atagagagaa | agagataaaa | 300 |
| agagaggaaa | gaattacgca | gacttaatat | ctgaccacca | aaacgacagt | ctacacacac | 360 |
| gccggttacg | gaaaagatga | gcgtcagagt | actgatcgcc | atttggcgat | cagatgtatt | 420 |
| ttcttcgcta | tcggnttata | ccgctccctc | tccgcttatt | ttgcgcagct | gacatgatcg | 480 |
| gcccgatcac | ttcgattcgt | tgtcgcaaga | tacgcgacaa | cttccaccag | ggtnttttgag | 540 |
| gtgattggca | tagttttagc | gnacgnnaga | tttacnccnn | tgngggcatt | tnttngggac | 600 |
| tttnntggac | catatataat | ttttgtgcac | tctctagttg | cattaatttg | tcatggcttt | 660 |
| tgattcacgc | gaatgttccc | cgacgcgaac | cgtttaatta | ttgtctgcgt | cataggatct | 720 |
| gtttcgcgtt | tgttctcgtc | tatatctatt | taacatcatc | ttcctttact | ccttgtcctg | 780 |
| tttgtctcgc | gcaatacgaa | atttttcacaa | agactgagac | gaagaatgcc | aacccgcaag | 840 |
| gctgagcgct | atgaaacccg | ccgagatcct | tgtgcgctga | tatttttgtg | cgcgttttcg | 900 |
| atggcgacgc | ccccaacgaa | cgctacggcc | caccgacgtg | cgggaaccgt | gaaatccaca | 960 |
| ccgcctccag | aggataaaca | tagctatacc | gcaaantact | atgacaaaga | catttatttt | 1020 |
| aacatttacg | aaggtngaag | ttctacgccg | aggggacgga | cgctatcgga | aatcatttct | 1080 |
| aaattttcta | cctccgaaat | gttangttta | aaaagngtta | aagcttggcg | taagccccnn | 1140 |
| a | | | | | | 1141 |

<210> SEQ ID NO 6
<211> LENGTH: 3979
<212> TYPE: DNA
<213> ORGANISM: Human herpes virus-6

<400> SEQUENCE: 6

| | | | | | |
|---|---|---|---|---|---|
| gtcgacgcga | cacacacaga | ggacgggcgg | acgcatctcg | gtccggcgca | acgaggcgag | 60 |
| actggcccac | gcgcgagccc | gtgcccgctt | cgactggctg | ctcctggccc | gcggcaggcc | 120 |
| gtccaaactg | tacggctatg | cgagccggca | tcgcggagaa | ctgatccacc | taccgtggcc | 180 |
| gccgtcctgg | tgtctagaac | tcaccacgat | ccgtacagag | cagccagaag | tgccaccgtg | 240 |
| tggggccacc | gctgggggttg | ccagcgacgc | acgtgagacc | cagatgcgtt | caagactgcg | 300 |
| gtgagtaaac | gtacgggcga | gccgcgggga | gggatgtcgg | tcagacagtg | agtgagtaca | 360 |
| aggttcgtcg | agaaccacca | gagacaccag | ccggtagaga | gtggggacaa | aaaaaaaacg | 420 |
| tcacgtcagg | ggccgcgagt | aacggaaaac | gagtatgaat | acgaggaggc | gagacgaaac | 480 |
| atagtcaagt | atgtgacgcg | ccggatcgta | aggcagtaaa | gccgatgacg | gcctccggcc | 540 |

-continued

| | | | | | |
|---|---|---|---|---|---|
| ccagagacga | ctcgcggagt | ggagtccagt | tattctattt | tttttgtgat | ttttttatc | 600 |
| cacaatccgg | tatccgtgaa | tccccgcaga | ggtactttcc | attaacgatg | gtacaggcgg | 660 |
| tataacttcc | ggaacacggt | cattacggat | atcctgtctc | gtttacgcga | gacctctttg | 720 |
| ttgtaatctc | ctataacggt | aaaaaaaaac | acaaagaaa | gattacagct | cctccttttt | 780 |
| tctgcgttat | ggcatcctcg | cattagtcac | cattcctgtc | gcgtgtgctt | ttcgctttga | 840 |
| attgtacgcg | acaggatacg | aatccgttat | actccaccag | ggcatagcga | ccacggctgt | 900 |
| atgcggcatc | tcccgttcca | cgggatgcct | ttgcgtgtgc | agatgttctg | tgcttttttt | 960 |
| atacggtcag | agaccacaga | caaaaataag | gcaacgccca | ccataacgtt | tatggtttct | 1020 |
| tgttgttttg | tttgcgttaa | acgcctcttc | tatcgtgtcg | gccggatcca | tcatcttcaa | 1080 |
| tcgttgacgt | acgcgcgtcc | catcacagcc | ctagactcct | gtctgtacgt | atgttgcgga | 1140 |
| tacggagaga | aacttcaacc | cgtgggtttc | gtaaagtcgt | atgtaaccaa | ctcccagctc | 1200 |
| gacacgctcc | gcgtcgctcc | tggtgggcaa | agacggagcc | gtgtacgtcc | accacactga | 1260 |
| gggcggcaag | actctgccga | ctggcgtcga | gcacaacgga | gtttacaaga | cgagggctgc | 1320 |
| aacgcgacgc | cgtgacgtat | gaagaagacc | tagagctgcc | ggaccagcgt | atgtgcggag | 1380 |
| cgaacgtccc | gacatctgtt | cgacgtgatc | gccgcggccg | ccgacgaaca | caacctgctg | 1440 |
| accgtcggcg | gcctgtgtca | gacgcacgcc | ggagtgtcct | gcaacttact | agagaccgtg | 1500 |
| ggagatccgt | ggacggcggt | tccggccgcg | cgcatgactc | tgaccgtgcc | gcaggttcag | 1560 |
| taccggttat | ggcccgaagc | ccggagagac | ctccgccggc | acctgtacgc | gggccacccc | 1620 |
| ctgggaccgt | ggctcgtgtg | cggcgttctc | tctcgagaga | gggagacgca | gaagccgtcg | 1680 |
| cctccgatac | gtacgactgt | gggaaacgta | ccaacgccgg | ggccacgcga | ggtggagatc | 1740 |
| gcttgggtgg | tcttgacttt | ggcgggacct | ctgttagcgt | tctggcccga | taccggcaag | 1800 |
| atctctcgtc | tggcaaactc | gttttccacc | ttatggaaga | tgggaccgcg | ggccatgaga | 1860 |
| ggacactgca | cgtactcggc | cccgggtaga | catctccccg | gggacgcgtg | gccactgtgc | 1920 |
| gaacacgtga | gaccgcaggt | gggaaagctt | ccgaggaaga | gagcgtacct | ggattagacg | 1980 |
| ccacggaggt | gaagtaagca | tgtcacctac | ggccagagac | gtgaccggag | gaaaatcatc | 2040 |
| catatgtgtg | ggtgtgtat | gcgtggggtg | cgtatgcgtg | cgcgtactcg | ttttccttcc | 2100 |
| ctcttcccctt | taaccccacg | aaaaataaaa | tccacgaacg | tagacagtca | cacacagggt | 2160 |
| gcttacgctc | cgtgttactg | atggcaggta | accaaaaaaa | cgtatctctc | ggccgtgatg | 2220 |
| caccgccgct | ctatagcgta | gtcgctatag | cagcgcccga | tgccaacgcg | acagggtgag | 2280 |
| tcacatagat | cgggactgct | tgaaagcgcg | tcgcgttcgc | ttcttatata | ggcaccccgg | 2340 |
| ggggtgggag | gagtgaacat | acaaaggagg | tgcgtccggg | attggaggca | aacgtagaaa | 2400 |
| acgaacagcg | tcagaaaaat | ataagaaaag | gcggagacac | atagccttgg | cgggaagacg | 2460 |
| acaacaggtt | taaaaataga | cagtcaaaaa | aatagcagac | tgtgacgtcc | aatacacatg | 2520 |
| tggcgatcat | ccaatcaacg | gggtgtatcg | aggcgcagac | acaaaagtat | gcggaagtac | 2580 |
| acacgacacg | gtaacgcgga | ccgaagacag | agggcgatcg | ctagcatggc | aagtgtaaga | 2640 |
| aaaaaaaaac | cacgttccaa | aaacacctat | acgggaaaca | tctcttcact | ccctccccgt | 2700 |
| cccaaccacc | gcaacattca | cctccgtaat | ccgttgtcac | cgcgtttcta | ccacggacgc | 2760 |
| gtacacacgc | agacacacag | acacgcacaa | cccacccatg | tggtagtcgc | gggtgggtac | 2820 |
| gtagatgggg | cataccgggg | tgagacgtga | agacaattca | aaacgacatc | gcgcgcgacg | 2880 |
| tgccaccgtc | tgggacccac | ggtcgcctgg | cacggtgcca | aaggaaacca | ccggctaacc | 2940 |

```
ctaaccctaa ccctaaccct aaccctaacc ctaaccctaa ccctaaccct aaccctaacc    3000
ctaaccctaa ccctaaccct aaccctaacc ctaaccctaa ccctaaccct aaccctaacc    3060
ctaaccctaa ccctaaccct aaccctaacc ctaaccctaa ccctaaccct aaccctaacc    3120
ctaaccctaa ccctaaccct aaccctaacc ctaaccctaa ccctaaccct aaccctaacc    3180
ctaaccctaa ccctaaccct aaccctaacc ctaaccctaa ccctaaccct aaccctaacc    3240
catcccccaa cgcgcgcgcg cacgccgcta tgggaggcgc cgtgtttttc accaacacgc    3300
gcgccgctgc gagagacgcg tgaaaaaaac tccccattgg ttgcggcccg agtcgccccg    3360
cgcgcggaag acacgcgtgt cgtggatgcg cgagcccccc cccgcacccc cccaaagagc    3420
ggacgacggt ataggggcgg acggcgcgta gtttaaaggc gaggtgagc gcgaagaacc    3480
gatggcgccg gcgagagaaa gagagagaga gacgggaggc agagccgcag agggcacacg    3540
aggatacgcc ggaggagaga gaacggccgc ggtcgttccc gaggagggcc cgcgcgcggc    3600
gcgagagagg gtgtagagcg gacgcgcgta gagacgcccc gccgggcggt tgacctttcc    3660
gcagacattt ttgcagaccc ccgacccgtg tcactgatgc aaacacgcgc gcgaacgtac    3720
acagacacgc cgacgcgccc caccgcgcag accgccacgt gagcgaaaac acacacgcgc    3780
gcgaaaaaaa aaacacacaa aaaaatacac acacgcaaaa aatacacac acgcgaaaaa    3840
aaataattta tgtatgcatt gttatcacga tgttaacata aacaacaac aataacaaca    3900
acaataacaa caaccacagc agcagcatta actacatcaa ctacattaac agacgaggac    3960
ggaatcaccg gatgtcgac                                                 3979
```

<210> SEQ ID NO 7
<211> LENGTH: 2084
<212> TYPE: DNA
<213> ORGANISM: Human herpes virus-6

<400> SEQUENCE: 7

```
aagctttatc ccaccggtcc ttcctcaaca tttacgcgtg gctgtctttg agtcgagggt      60
ctccgcgaaa agtgtacgga tatgccttca ggcacacagg agaactcgta gcattgccat     120
ggccgcctaa ctggagcctg gaacttcacc acgatcccta tcgagacgcc agaccacaaa     180
ccgtttggag tcaccgctgg ggatggcctg caacacacgt gacagctcgc acggtgcggg     240
actgcggtga gtgtaagcag tgtgacacat tgttatcgca attgtcttac ccgattaact     300
tтттатттaат gtattaagca ctctttcttc acgtgtgact gttgtgtttt tgttgttat     360
ctacatcccg gcagccctcg acacgcatat gtacgtgtgc tgcggacgcg gagaaaagtt     420
gcagcccgtc ggatacgtac gcaacagagc gcgccttca gacctgaact cgttacgcgt     480
cctcctcata gccagggacg gagcaatgta tgtgcatcac atgagaacgg cgcgactgtg     540
ccgcctagcc agcagtgtga ccgaattcgc gcgacgaggg ctgcagcgag aatccgaggt    600
ttatgaagat gатgттттcстт tgccagaccg tcgattaggt tcggcaacgg ccattcacct    660
gtttgacgta attacccagg cagccgatgt ccacgaccta ctcaccgtgg ccggactgtg    720
tcagactcac accggcgtca gctgccaact gtggtataca gaccacgatc cccacaccgt    780
cgctgggcg gcacgcttca cactgacggt cgcacggcag cagtatcgat tgtggccaaa    840
cgcacgacgc aaactgctgc agcacctaca tccggaccac ccacttgggc tgtggctgtt    900
gtgtgccgtg ctcacgtacg atgcaaaaga gacgaatcgc gcagtgccac ccgtaacgcc    960
aggggccgaa accgtgtggg tgatagttac tggcaggggt gccattctag gattctggcc   1020
```

```
                                        -continued agagagcgcc aaaatgtgca gattggcctc gtctatgaaa ggactctgga aaaacggagc    1080
ccgggcgcta aaaatgtgca gattggcctc agcacccggc cggcatagag cgggagaggc    1140
ctggcctttg tgtgcacact accaatctcc tagatacaaa aaaattaaaa agattaaaaa    1200
aaaaaagaaa aaaagtacaa gagtgttatc gcgaaacagc gtgtcaaaaa aaaaaacaat    1260
ccacatactc tagaacaaac tgtacccaaa aataagtccg tgtgcaaaac tgggaaaaaa    1320
aaaatcacct tcctcgttgc cactagaggg agtaccgaaa gtgtaggcaa gaaggccacg    1380
ctgtaaatga ctgtcagcgt ttggcgctga aaacattgct gttcttgctg gctcaagcac    1440
aatcacgtga ttaagattcc tttcgttttc aaagtgtgcc cgggcggcag acatgccctt    1500
tctcgtgaga cattatgaga tttgcctgcc agagaaccac gtgacttgga cttactttcg    1560
ttttctaaac gtgccctcta ggcatgaatg ctctttagcg ttagccatga ggctagcgtg    1620
atcctgtata gtacataagt ttctaagaat atgtttttaa caataatcat gtcccaaaaa    1680
gtcgcgagtg actaaaattc tctgtaaatg aaggcaaatt aaacaggata cagacagttg    1740
tggcagtggt ccgtttcgtc tttctgtgtt ttccttacgc ggctgacgag gtaaagtgtc    1800
tcagtccata ttgttgtctg tgccaccgta gttagcggtg gcatactaaa aactccgata    1860
gatgcagaac aataacaccg aaaaccacgc tgtggaacca gaccagactt tataaacaaa    1920
acggccttat cacctggaaa aaaaaactaa aaataaggca atgatacacc tgactttcca    1980
ttggaaacct gccgtaaccc tgaccacaaa tcccatgcta aatccactga aacactgcca    2040
aacgtcgcta caaggttttt ccgggatcga gccgcagcaa gctt                    2084
```

LYMPHOTROPIC AGENTS AND VECTORS

FIELD OF THE INVENTION

The present invention is generally in the field of targeted therapeutic agents. By one of its embodiments, the present invention concerns an agent which specifically binds to receptors on certain cells. By a second embodiment the present invention concerns vectors specifically targeted to certain cells.

A specific aspect of the present invention concerns the prophylaxis and treatment of AIDS.

PRIOR ART

The following are references considered to be relevant for the subsequent description.

1. Salahuddin, S. Z., Ablashi, D. V., Markham, P. D., Josephs, S. F., Sturzenegger, S., Kaplan, M., Halligan, G., Biberfeld, P., Wong-Staal, F., Kramarsky, B., and Gallo, R. C. Isolation of a new virus, HBLV, in patients with lymphoproliferative disorders. *Science*, 234:596, 601, 1986.
2. Schirmer, E. C., Wyatt, L. S., Yamanishi, K., Rodriguez, W. J., and Frenkel, N. Differentiation between two distinct classes of viruses now classified as human herpesvirus 6. *Proc. Natl. Acad. Sci.*, USA, 88:199–208, 1991.
3. Frenkel, N., Roffman, E., Schirmer, E. C., Katsafanas, G., Wyatt, L. S. and June, C. Cellular and growth factor requirements for the replication of human herpesvirus 6 in primary lymphocyte cultures, in: Immunology and Prophylaxis of Human Herpesvirus Infections, eds. Lopez, C., Mori, R., Roizman, B. and Whitley R. J., Plenum Publishing Corp. pp 1–8, 1990.
4. Kondo, K., Kondon, T., Okuno, T., Takahashi, M. and Yamanishi K. Human herpesvirus 6 infection of human monocytes/macrophages. *J. Gen. Virol.* 72:1401–1408, 1991.
5. Lusso, P., Ensoli, B., Markham, P. D., Ablashi, D. V., Salahuddin, S. Z., Tschachler, E., Wong-Staal, F., and Gallo, R. C. Production dual infection of human CD4$^+$ lymphocytes by HIV-1 and HHV-6, *Nature*, 337:370–373, 1989.
6. Frenkel, N., Schirmer, E. C., Wyatt, L. S., Katsafanas, G., Roffman, E., Danovich, R. M., and June, C. H. Isolation of a new herpesvirus from human CD4$^+$ T cells. *Proc. Natl. Acad. Sci.*, USA, 87:748–752, 1990.
7. Wyatt, L. S., Rodriguez, W. J., Balachandran, N., and Frenkel, N. Human herpesvirus 7: antigenic properties and prevalence in children and adults. *J. Virol.*, 65:6260–6265, 1991.
8. Wyatt, L., and Frenkel, N. Human herpesvirus 7 is a constitutive inhabitant of adult human saliva. *J. Virol.* 66:3206–3209, 1992.
9. Pellett, P. E., Lindquester, G. J., Feorino, P., and Lopez, C. Genomic heterogeneity of human herpesvirus 6 isolates. *Adv. Exp. Med. Biol.* 278:9–18, 1990.
10. Lawurence, P. J., Chee, M., Craxton, M. A., Gompels, U. A.,Honess, R. W., and Barrell, G. B. Human herpesvirus 6 is closely related to human cytomegalovirus. *J. Virol.* 64:287–299, 1990.
11. Lindquester, G. J., and Pellett, P. E. Properties of the human herpes-virus 6 strain Z29 genome: G+C content, length, and presence of variable-length directly repeated terminal sequence elements. *Virology*. 82:102–110, 1991.
12. Martin, M. E., Thomson, B. J., Honess, R. W., Craxton, M. A., Gompels, U. A., Liu, M. Y., Littler, E., Arrand, J. R., Teo, I., and Jones, M. D. The genome of human herpesvirus 6: maps of unit-length and concatemeric genomes for nine restriction endonucleases. *J. Gen. Virol.* 72:157–168, 1991b.
13. Frenkel, N., and Wyatt, L. S. Human herpesviruses 6 and 7 as exogenous agents in human lymphocytes. *Develop. Biol. Standard.* 76:259–265, 1992.
14. Lopez, C., Pellett, P. Stewart, J., Coldsmith, C., Sanderlin, K., Black, J., Warfield, D. and Feorino, P. J. *Infect. Dis.*, 157:1271–1273, 1988.
15. DiLuca, D., Katsafanas, G., Schirmer, E., Balachanran, N. and Frenkel, *N. Virology*, 175:199–210, 1990.
16. Frenkel, N., Schirmer, E. C., Wyatt, L. S., Katsafanas, G., Roffman, E., Danowich, R. M. and June, C. H. *Proc. Natl. Acad. Sci.*, USA, 87:748–752, 1990.

Human herpes virus-6 (HHV-6) was first isolated from peripheral blood mononucleur cells (PBMC) of patients with lympho proliferative disorders as well as from patients suffering from acquired immune deficiency syndrome (AIDS) (Salahuddin et al. 1986).

Two types of HHV-6 strains are recognized today and designated as variant A and variant B which differ as regards to their growth properties, restriction enzyme patterns and antigenicity and they are also distinct epidemiologically (Schirmer et al., 1991). Only the HHV-6 B variant appears to be associated with human disease and has been found to be the causative agent of exanthem subitum (ES, roseola infantum).

HHV-6 is shown to replicate only in interluken-2 (IL-2) activated T cells (Frenkel et al., 1990) and is inhibited by very high concentrations of IL-2. After the initial infection process, the HHV-6 virus undergoes a latency period in the infected cells (Kondo et al. 1991).

Recently, it has been shown that HHV-6 may effect the efficiency of expression of the human immunodeficiency virus-1 (HIV-1) when the two viruses have infected a single cell (Lusso et al., 1989).

Human herpes virus-7 (HHV-7) is a DNA virus first isolated in the laboratory of the inventor of the present invention from activated T cells expressing the CD4 antigen (see U.S. Ser. No. 07/553,798 and Frenkel et al., 1990). Cells expressing this antigen on their membrane will hereinafter be referred to as "CD4$^+$ cells".

HHV-7 was found to be distinct, both molecularly and antigenically, from all previously identified herpes viruses. HHV-7 replicates well in lymphocytes and particularly in T cells including CD4$^+$ T cells and possibly other cells carrying the CD4 marker. The HHV-7 virions specifically target the T cells wherein the viral DNA is synthesized in the nucleus as concatemers which are then cleaved and packaged into structural infectious particles. It has been shown recently that HHV-7 binds specifically to the CD4 receptor by which it infects CD4$^+$ cells.

HHV-7 is found in sera of more than 95% of humans (Wyatt et al., 1991). In addition, the virus is very often found in human saliva (Wyatt et al., 1992). No known disease is associated with HHV-7 and no symptoms have been discovered in individuals infected by the virus at early childhood.

HHV-6 and HHV-7 DNA comprise a long unique sequence which is flanked by terminal direct repeats (TR) on each side (Pellet et al., 1990, Lawrence et al., 1990, Lindquester et al., 1991 and Martin et al., 1991). Each TR contains on one side a sequence which is heterogenous in size, designated het. The het sequence was thought to be a variable and unstable sequence but later was found to be a unique sequence for each virus strain and to remain stable in a single strain over many passages of the virus (Schirmer et al., 1991). On the other side of the TR there is a repeated telomeric-like sequence having repeated units of the sequence GGGTTA.

CD4$^+$ cells are also the target cells of the human immunodeficiency virus (HIV) which is the cause of acquired immuno deficiency syndrome (AIDS).

HIV binds to the CD4 receptor on the target cell with a high affinity, integrates itself into the host cells' genome and is believed to undergo a long latency period during which it is virtually undetectable. Activation of the virus to induce the disease may occur at different time periods after the first infection.

Many attempts have been aimed at delaying or inhibiting the activation of the latent HIV in an infected individual. Such attempts include various treatments targeted at inhibiting the HIV's regulatory replication and structural proteins, e.g. Tat and Rev or by down regulation of these or other regulatory proteins of HIV. Examples of such treatments include the use of the drug AZT, both alone or in combination with other drugs such as ddI and nevipapine and methods of gene therapy by the use of an RNA virus vector.

In addition to treatments such as the above, research has centered mainly in trying to immunize individuals against infection or against a spread of HIV in the body of already infected individuals. For this purpose, both classic vaccination approaches as well as the use of various genetically engineered immunogens have been tested, but to date, none of these vaccination approaches have been found effective.

GENERAL DESCRIPTION OF THE INVENTION

It is an object of the present invention to provide novel lymphotropic agents, i.e. agents capable of exerting therapeutic effects on lymphatic cells.

It is more specifically an object, in accordance with a first embodiment of the present invention, to provide a ligand capable of binding to the CD4 receptor (hereinafter: "CD4-ligand"). Such a ligand is useful for inhibiting the infectious process of viruses which infect the CD4$^+$ cells and which enter the cells by first binding to the CD4 receptors. Another possible use of the CD4-ligand is as an immunomodulating agent.

It is more specifically an object in accordance with a second embodiment of the present invention to provide a DNA vector specifically intended for lymphatic cells (hereinafter: "lymphotropic vector"). Specific applications of the lymphotropic vector are in the treatment of AIDS as well as in the treatment of lymphatic malignancies, various autoimmune disorders, as well as a variety of T-cell pathologies.

Other objects of the present invention are the provision of pharmaceutical compositions and methods making use of the CD4-ligand or lymphotropic vector.

In accordance with a first embodiment of the present invention, there is provided a CD4-ligand, selected from the group consisting of:

(a) human herpes virus 7 (HHV-7);
(b) a mutant of HHV-7 capable of binding to the CD4 receptor;
(c) a virus particle of the virus of (a) or (b);
(d) a virion polypeptide of (c) capable of binding to CD4 receptor;
(e) a fusion protein of a fragment of (d) and another protein or peptide, which is capable of binding the CD4 receptor;

(f) derivatives of any of (c), (d) or (e) obtained by chemical modification, addition, deletion or replacement of one or more amino acid residues from the protein or peptides of (c), (d) or (e) which are capable of binding to the CD4 receptor; and
(g) any combination of the agents under (a), (b), (c), (d), (e) and (f).

In accordance with a second embodiment of the invention, there is provided a lymphotropic vector comprising a recombinant DNA molecule having:

(i) a DNA sequence derived from HHV-6 or HHV-7 and comprising an origin of DNA replication, a promoter sequence capable of inducing expression in a lymphatic host cell of a downstream nucleic acid sequence and a cleavage and packaging signal;
(ii) a foreign nucleic acid sequence downstream to an expression control of said promotor sequence.

For therapeutic use, said lymphotropic vector is incorporated into a delivery vehicle. A large number of vehicles are available for the delivery of genetic material into cells, delivery vehicle which are viral-derived particles are generally preferred in view of the specificity of such particles to certain cells which facilitate the targeting of the genetic material to such cells. Seeing that the lymphotropic vector of the invention is derived from HHV-6 or HHV-7, the preferred viral particle for use as a delivery vehicle is derived from these two respective viruses. There is some evidence that HHV-7 may activate HHV-6 replication (Frenkel et al. 1992), and accordingly, it is also possible in accordance with the invention to use an HHV-7 particle as a delivery vehicle for an HHV-6 derived lymphatic vector.

HHV-6 or HHV-7 particles have an affinity to specific cell types. The HHV-7, binds to the CD4 receptor and accordingly the particle derived from the HHV-7 is particularly useful for the delivery of said lymphotropic vector to CD4$^+$ cells. The HHV-6 particles have an affinity to a variety of cells and mainly to both CD4$^+$ and CD8$^+$ cells, as well as to some other lymphatic cells, e.g. EBV infected B-cells, and may thus be useful for the targeting of said lymphotropic vector to such cells.

The preferred delivery vehicle in accordance with the present invention, is a member selected from the group consisting of:

(a) an HHV-6 or HHV-7 particle;
(b) a mutant HHV-6 or mutant HHV-7 particle capable of infecting lymphatic cells and delivering its content of DNA to such cells;
(c) a chemically modified particle of (a) or (b) essentially retaining the ability to infect lymphatic cells; and
(d) any combination of (a), (b) or (c).

It should be noted that the use made above and below of the term "lymphotropic vector" is only for convenience and does not mean to indicate that the vectors are limited only to lymphatic cells. As readily known, there are non-lymphatic cells which are CD4$^+$, e.g. fibroblasts or various brain cells, and said vector, using HHV-7 as a delivery vehicle is thus useful also as a therapeutic agent targeted at such non-lymphatic CD4$^+$ cells. Similarly, HHV-6 is known to be capable of infecting also non-lymphatic cells, e.g. fibroblasts, CD4$^+$ brain cells, endothelial and epithilial cells and accordingly may be used as a therapeutic agent targeted also at such non-lymphatic cells.

Specific applications of said ligand or said lymphotropic vectors is in the treatment and/or prophylaxis of viral diseases which infect lymphatic, specifically CD4$^+$ or CD8$_+$, cells. An example of such an application is in the treatment and/or prophylaxis of HIV infections, in the treatment and/or prophylaxis of lymphomas or various autoimmune-related diseases or disorders, in the treatment of various T-cell pathologies, etc.

The present invention thus provides a pharmaceutical composition comprising a pharmaceutically acceptable carrier and, as an active ingredient, either said CD4-ligand or said lymphotropic vector. The present invention still further provides a method for the treatment of a disease or disorder comprising administering said CD4-ligand or said lymphotropic vector to an individual in need.

Said CD4-ligand may be used in order to inhibit infections of CD4$^+$ cells which progress through the binding of the infectious agent to the CD4 receptor. A notable example of such is in the treatment of HIV infections. In addition, said CD4-ligand may also be used as an immuno-modulator, e.g. as a general immunosuppressor in autoimmune diseases.

Said lymphotropic vector is useful as an agent for genetic therapy in the treatment of various malignancies, viral infections, enzyme deficiencies and others, of lymphatic cells as well as other cells capable of being infected by HHV-6 or HHV-7. Two kinds of vectors are provided by the present invention: a vector which is capable of autonomous replication (hereinafter: "ARV" (autonomously replicating vector)); a vector which is not capable of self replication (hereinafter: "Tamplicon"). While an ARV can be administered by itself, a Tamiplicon is administered together with a helper virus which provides the transactivation factors for replication of the Tamplicon. A helper virus is typically a self-replicating HHV-6 or HHV-7. The choice of the helper virus may typically be based on the nature of the Tamplicon: in case of a Tamplicon derived from HHV-6, a self-replicating HHV-6 will typically be used, and in the case of a Tamplicon derived from HHV-7, a self-replicating HHV-7 will typically be used. As pointed out above, a self-replicating HHV-7 may be used as a helper virus for an HHV-6 derived Tamplicon.

As already pointed out above, HHV-7 has no known pathology and therefore its use as a helper virus is generally preferred where possible over the use of HHV-6. However, use of HHV-7 is limited in view of the fact that it infects primarily CD4$^+$ cells and accordingly use of HHV-6 is at times preferred. In case use is made of the HHV-6, measures should be taken to neutralize this virus after such period of time. Alternatively, a mutant HHV-6 may be used, the expression of which may be controlled by changes in various factors such as, a change in temperature (i.e. a temperature sensitive mutant).

BRIEF DESCRIPTION OF THE DRAWINGS

FIG. 5a, SEQ ID NO:1, shows the sequence from the pac-2 U1102 left terminus, FIG. 5b, SEQ ID NO:2, shows the sequence from the pac-2 unique sequence junction and FIG. 5c, SEQ ID NO:3, shows the sequence from pac-1.

FIG. 6 shows het sequences from the Z29 B substrain of HHV-6; FIG. 6a SEQ ID NO:4 shows the sequence from the HindIII site and FIG. 6b shows the sequence from the pst site.

FIG. 7 SEQ ID NO:6 shows the 4 Kb insert of pNF1022, which is a clone of HHV-6;

FIG. 8 SEQ ID NO:7 shows the 2.1 Kb insert of pNF2009 (HA9), which is a clone of HHV-7;

DETAILED DESCRIPTION OF THE INVENTION

Figure 1:
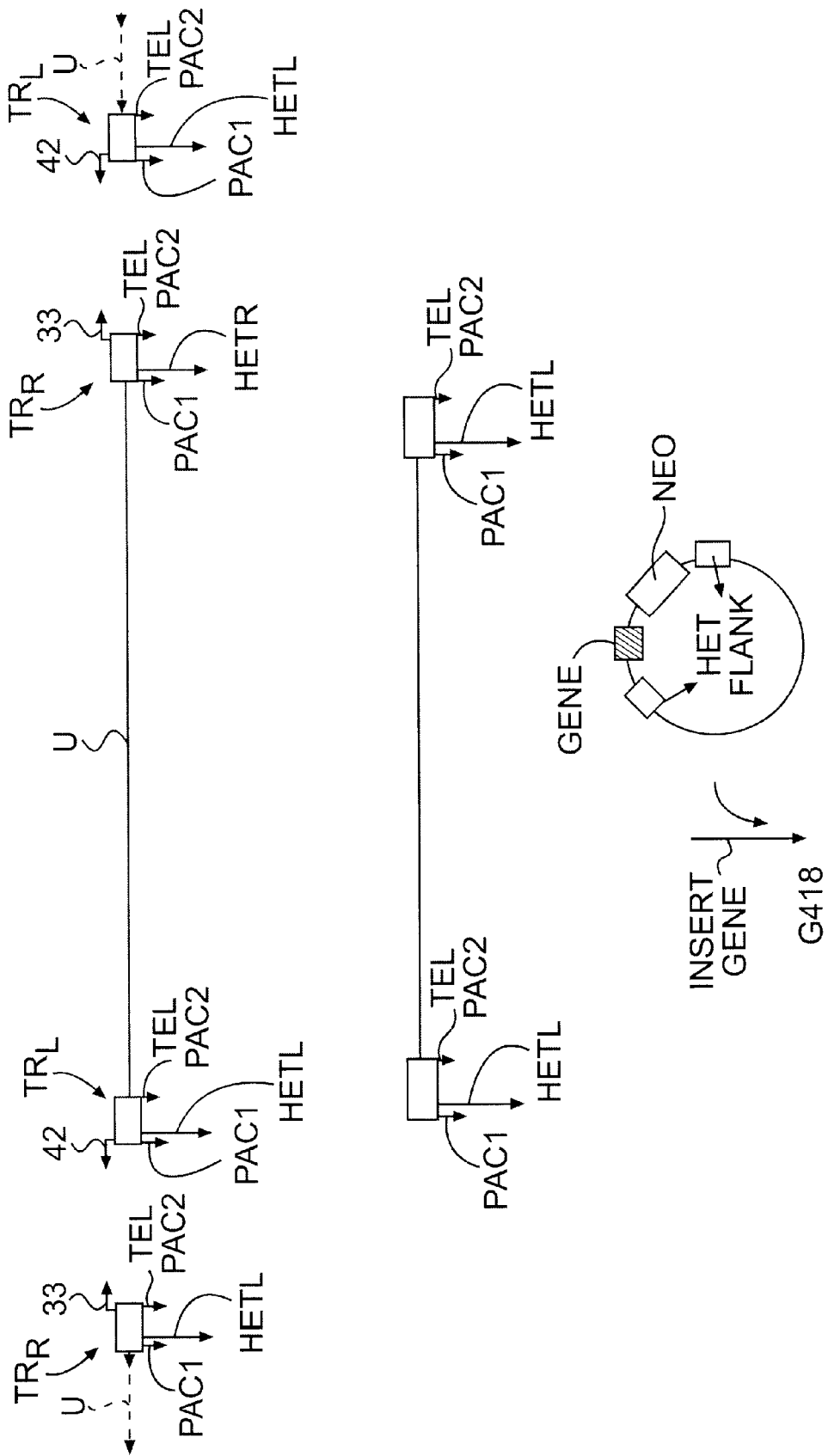
FIG. 1 is a schematic representation of the genome of HHV-6 or is HHV-7. The figure shows a unit length of the genome as well as cleavage sides enabling to cut the expressed DNA into unit length sequences and the packaging thereof into a viral particle.

In accordance with the present invention novel lymphotropic agents, as defined above, are provided, useful for the treatment and/or prophylaxis of various diseases or disorders, particularly lymphatic diseases or disorders. The present invention has two embodiments, a first embodiment involving the use of said CD4-ligand and a second embodiment involving the use of said lymphotropic vector. Each of these two embodiments will be separately detailed below.

In the description below reference will at times be made to specific therapeutic indications which should not be construed as limiting the scope of the invention.

I. The First Embodiment

Said CD4-ligand is useful for protecting individuals against primary infection by viruses which are targeted to CD4 receptors, notably the HIV virus, the causative virus of AIDS. For this purpose, said CD4-ligand may be administered to individuals which are at high risk of encountering such infections. The CD4-ligand may also be administered to individuals already infected by said virus, in which case it may protect non-infected CD4$^+$ cells from infection by the HIV.

HHV-7 has no known pathogenicity, namely, there are no known diseases associated with this virus. Accordingly, the intact HHV-7, or a weakened variant thereof may be used as said CD4-ligand. Additionally, also mutants of HIV-7 may be used as said CD4-ligand.

A mutant HHV-7, as defined in the definition of said CD4-ligand under (b) above, may be obtained by standard methods. An example of a mutant is such which lost its ability to replicate by itself in a host cell. Another type of mutant may, for example, be such which has a higher affinity to binding to the CD4 receptor than the native strain.

A particle of the virus, as defined in the definitions of said is CD4-ligand under (c), may be obtained by various standard methods which are known in the art. Various polypeptides, as defined under (d), are obtainable either by chemical methods or by methods of genetic engineering, namely, by cloning and expressing a gene coding for the polypeptide. Such a polypeptide is typically a portion of the capsule which determines the binding affinity of the capsule to the $CD4^+$ receptor. Polypeptides produced by means of genetic engineering are very often obtained as fusion proteins of the desired polypeptide with another protein or peptedic component. Such fusion proteins, defined under (e), may also be useful at times as said CD4-ligand.

Derivatives as defined in the definition of said CD4-ligand under (f), may be obtained by various standard chemical or biochemical methods, or by methods of genetic engineering, such methods being generally known per se.

Said agent may be useful for both in vitro or in vivo applications. In vitro applications may, for example, be in laboratory use, in labelling $CD4^+$ cells, in which case said agent will be conjugated to a detectable marker (fluorescent marker, radioactive marker, enzyme marker, chemiluminescence marker, etc.). In vivo applications include various therapeutic applications as already pointed out above.

For in vivo use, a certain constant level of said agent should be retained in the blood. The advantage of said agent as defined under (a) and some of said agents as defined under (b) is in that they have self-replicating properties and can thus replicate autonomously within the individual. Consequently, said agents (a) and (b) will retain a certain constant level in the blood. Against this, said agent under (c)–(f) have to be administered continuously in order to retain a certain level thereof in the blood.

II. Second Embodiment

In accordance with the second embodiment, said lymphotropic vector is administered to cells for genetic modification of these cells. The said lymphotropic vector may be administered in vivo, or may be applied to cells ex vivo. An example of ex vivo use is in infection of lymphatic cells which are removed from the body. Various therapeutic protocols used today call for the withdrawal of lymphatic cells, modification of the cells ex vivo and then return of the modified cells into the body where the modified length lymphatic cells exert a therapeutic effect. In accordance with the invention, withdrawn lymphatic cells are infected with said lymphatic vector wherby they become genetically modified upon which they may be returned to the body.

In in vivo use, a patient is administered with said lymphatic vector, typically packaged in a matching viral particle. Where said vector is an RDV, it is administered together with a self-replicating HHV-6 or HHV-7, as the case may be.

The nature of said foreign nucleic acid sequence depends on the desired therapeutic indication. In the case of AIDS therapy, said foreign DNA sequence may, for example be one of the following:

(a) a DNA sequence encoding a toxin which is under expression control of a Tat activated promotor, in which case, the toxin will be expressed in HIV infected cells in which the Tat protein is expressed.

(b) An antisense sequence to a sequence of the HIV genome which is essential for its replication, e.g. the tar site at the HIV LTR.

(c) A DNA sequence encoding an inhibitor of a structural or a regulatory protein of the HIV.

Said lymphotropic vector may also be used for other indications including the treatment of enzyme deffeciencies, in which case said foreign nucleic acid sequence will encode the missing enzyme. An example is in the treatment of Gaucher disease in which there is a glucocerebrocidase deficiency. Another example is supplementing deficiencies in insulin and insulin-like growth factors, missing in diabetic patients because of the lack of pancreas beta cells. In the treatment of diabetic patients, said foreign and nucleic acid sequence may be placed under control of a promoter, the activation of which is contingent on the glucose level. In such cases, controlling the level of expression of the foreign sequence is necessary in order to prevent situations of harmful over-production of the specific enzyme or protein. Such control may be achieved by use of a lymphotropic vector comprising a second foreign sequence encoding the Thymidine Kinase (TK) enzyme. HHV-6 and HHV-7 are insensitive to antiviral drugs such as Acyclovir™ (Wellcome, U.K.) and once the vector is made to express also TK, expression thereof together with the viral DNA polymerase renders the cells infected with HHV-6 sensitive to Acyclovir. It then becomes possible to stop the expression of said first foreign sequence when necessary by use of Acyclovir.

Another indication for which said lymphatic vector may be used is for the treatment of lymphomas. The lymphotropic vector for use in this indication may either contain a nucleic acid sequence which encodes a product which either destroys or inhibits proliferation of malignant cells or, alternatively, encodes an expression product which protects non-malignant cells from the toxic effect of chemotherapeutic agents or radiation.

Malignant cells are very actively replicating cells, and although the lymphotropic vector of the invention is not discriminatory, namely, it infects both malignant and non-malignant cells, in view of the activity of the malignant cells, said nucleic acid sequence will be expressed mainly in the cells. Said foreign nucleic acid sequence may encode a toxin protein which will be expressed mainly in the malignant cells and consequently these cells will either be inhibited or die. As another alternative, said foreign nucleic acid sequence may have an antisense sequence of an oncogene active in these cells or may encode a product which will interfere in the cancerous process. As a further alternative, said foreign DNA sequence will encode the product which will increase the cells' sensitivity to chemotherapy.

A specific example of the latter alternative is the use of a lymphotropic vector as described above wherein said foreign nucleic acid sequence encodes the enzyme Thymidine Kinase (TK). Infection of the cells with such a vector; and the higher expression of the TK in the malignant cells infected with this lymphotropic vector versus a relatively low expression of the TK in non-malignant cells, will render the malignant cells sensitive to Acyclovir which can then be used as a chemotherapeutic agent for the treatment of T-cell malignancies.

The lymphotropic vector of the invention may also be used for infection of lymphocytes ex vivo. Therapeutic techniques involving the withdrawal of lymphocytes, the treatment of withdrawn lymphocytes and the return of these to the body are well known, example being the reintroduction into the body of IL-2 treated T-infiltrating lymphocytes (TIL). In accordance with this embodiment, TIL, as well as other kinds of lymphocytes, are infected ex vivo by the lymphotropic vector, with the aim of modifying their biological activity to be manifested once they are returned to the body. If desired, the infected lymphocytes may first be subject to selection whereby only the infected lymphocytes will then be returned to the body. This may be achieved, for example, by the use of a marker such as the neo gene which confers ability to grow in a selection medium containing the antibiotic G418.

ex vivo infection of TIL may also be useful for various imaging applications. The lymphotropic vector, in accordance with such an embodiment, carries a gene encoding a detectable marker. The TIL, after return to the body, are attracted to tumor sites, and consequently the marker will be localized in such sites which may provide a way to identify a tumor and its metastisis.

In all such cases, the expression of said first nucleic acid sequence in the infected lymphocyte may be controlled by using a vector comprising a second foreign sequence encoding the TK enzyme, in a similar manner to that described above.

Another indication for which said lymphotropic vector may be used is in the treatment of autoimmune diseases or disorders. In autoimmune diseases, specific clones directed against self antigens are activated and start to divide. The treatment of autoimmune diseases will be similar, in principle, to the treatment of malignancies, e.g. use of said lymphatic vector wherein said nucleic acid sequence encodes the enzyme TK.

An example of an autoimmune indication, which can be treated by the use of the lymphotropic vector of the invention, is multiple sclerosis (MS). In MS patients the myelin basis protein (MBP) is degraded as a result of attack by the patient's immune system. Example of therapy of such patients is intramuscular injection of COP-1™ (Teva Pharmaceuticals, Israel) wherein the active ingredient consists of a random assembly of oligopeptides corresponding to MBP. In accordance with the present invention, lymphocytes can be treated to express the COP-1™ oligopeptides by ex vivo or in vivo infection. The expressed COP-1™ oligopeptides will be released to the bloodstream and will then act in a similar manner to injected COP-1™ oligopeptides. Here again, control of expression of the foreign sequence in the lymphotropic vector may be achieved by the use of an additional foreign sequence encoding the TK enzyme and treating the individual with Acyclovir, in a similar manner to that described above.

It is known that the het sequences remain constant in a single variant over many in vitro passages of the virus. Seeing that the het sequence has no involvement in the replication of the virus, it is a preferred target for incorporation of said foreign nucleic acid sequence.

As can be seen in FIG. 1, the HHV-6 or HHV-7 consist of several genes, represented herein schematically as the unique sequence U, and at its right and left side two terminal repeats, TRR and TRL. Each of the teriminal respeats comprises a pac-1 and pac-2 site. The viral genome is expressed as a concatemer comprising a plurality of repeats of the basic sequence and is then cleaved at a site which is formed from the combined pac-1 sequence of $LTR_L$ and the pac-2 sequence of an adjacent $TR_R$. The site required for such a cleavage includes about 42 bases from $TR_L$ and 33 bases from $TR_R$.

Figure 2:
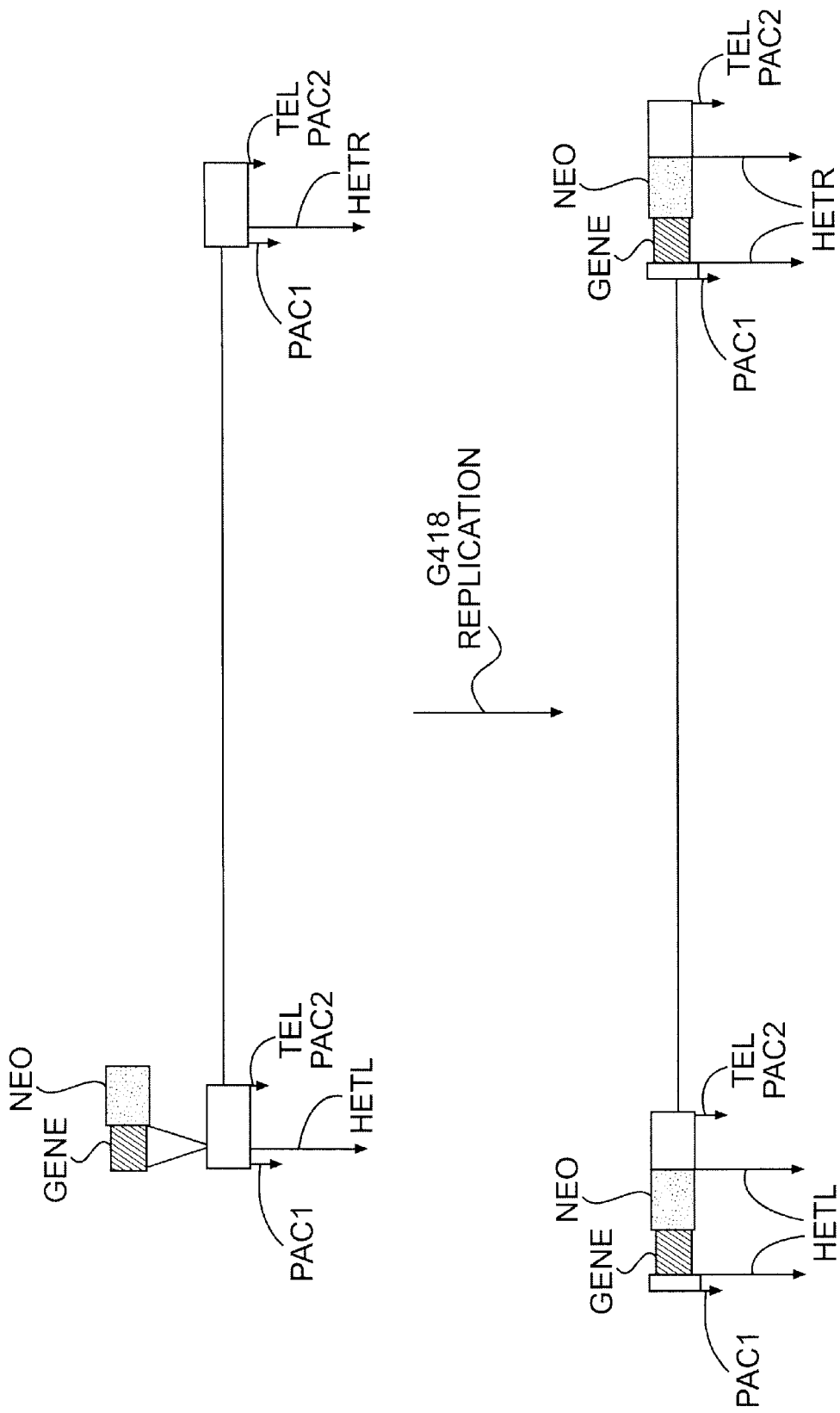
FIG. 2 is a schematic representation of an example of an ARV in accordance with the invention.

FIG. 2 shows an ARV in accordance with the invention. A plasmid comprising a foreign nucleic acid sequence, referred to in the figure as "gene", having an attached selection gene, "neo" in the specific example, is recombined with the HHV-6 genome by cotransfecting the HHV-6 and the plasmid into a host cell, e.g. a T cell. Said gene with the attached selection gene, is flanked by its two ends by a het sequence identical to the het sequence of the viral genome and consequently, this nucleic acid section becomes incorporated into the hat sequence of the viral genome. Following selection under conditions allowing survival of only cells containing the selection gene, and several replications in host cells, a lymphotropic vector is formed containing said gene in its two het sequences.

Figure 3:
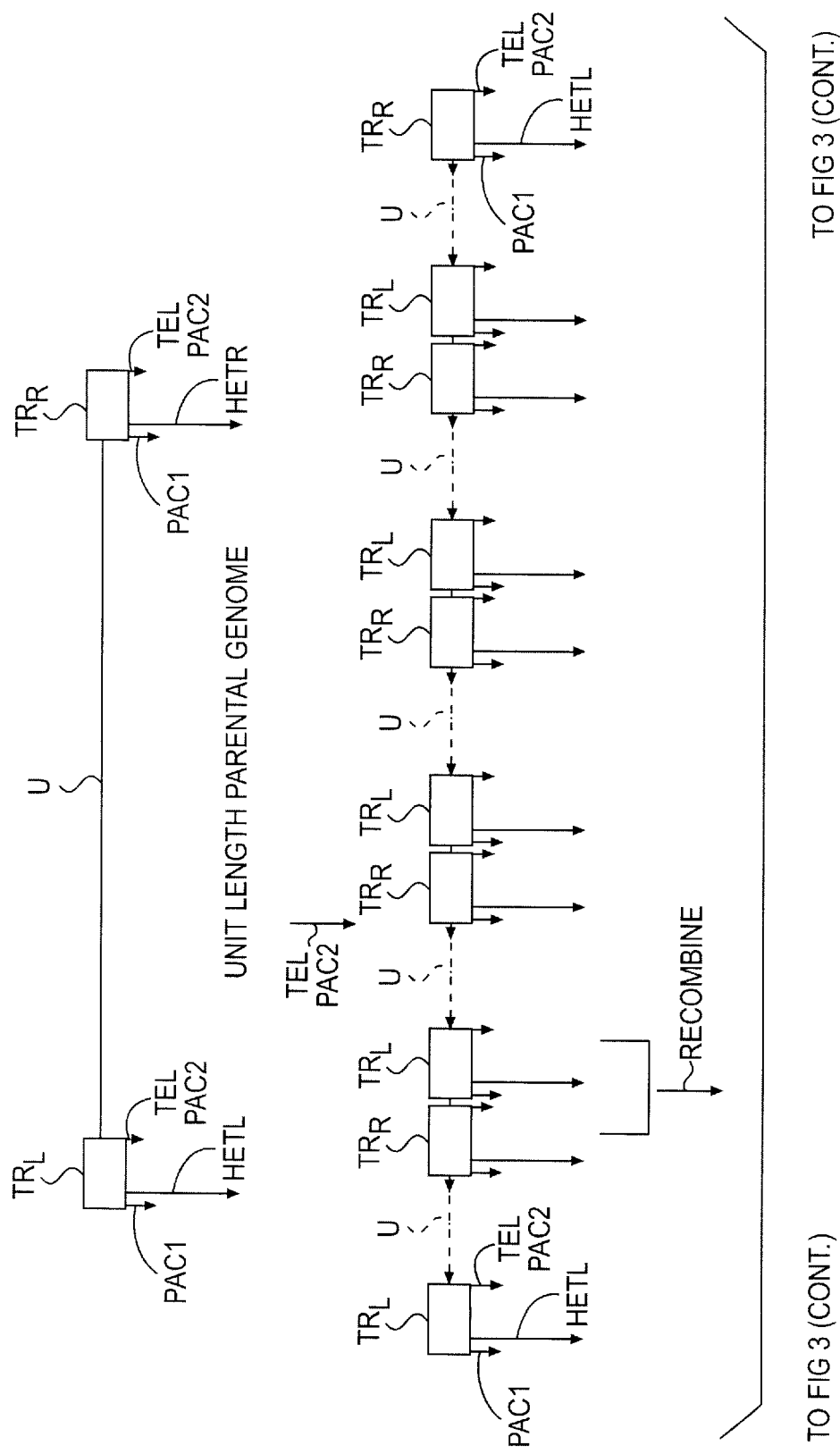
FIG. 3 shows the formation of concatemers during replication of the HHV-6 or HHV-7 genome and the manner in which the concatemer is cleaved to individual unit length genome.
Figure 3:
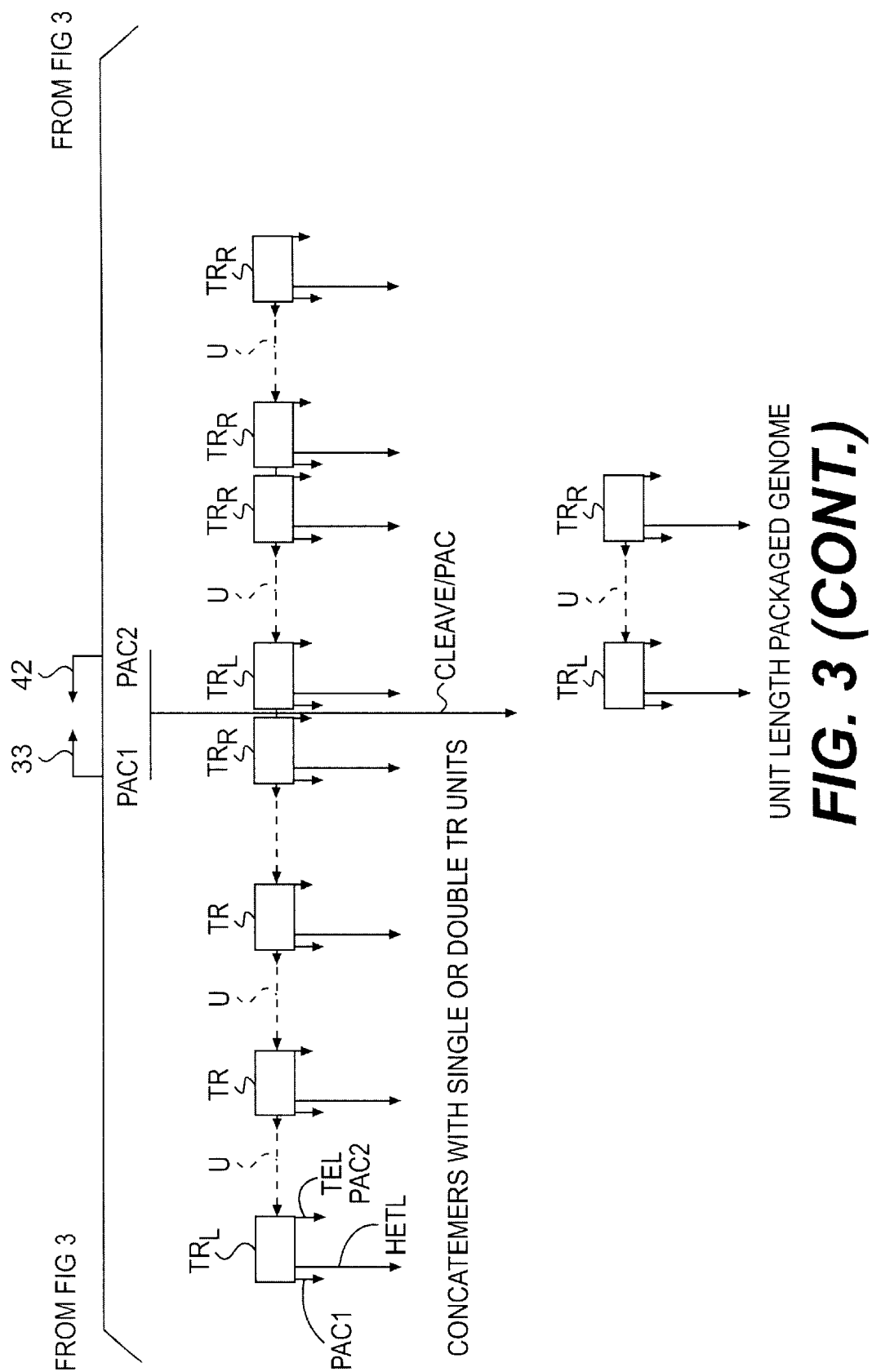

Reference is now made to FIG. 3 which is a schematic representation of the manner of replication of an HHV-6 or HHV-7, discovered in accordance with the invention. The viral genome (A) is replicated as a concatemer consisting of a plurality of basic genome units bound to one another. From the concatemer, said genomic units are formed by cleavage occurring between pac-1 and pac-2 in the manner shown in FIG. 1.

In view of homology of about 10 kilobases in $TR_L$ and $TR_R$, the two often recombine and consequently a concatemer having a single terminal repeat for each concatemer unit is formed. In this case, cleavage is not possible and accordingly replication becomes inhibited. This recombination does not occur in all instances and where their recombination does not occur, the single units can be cleaved out from the concatemer.

Figure 4:
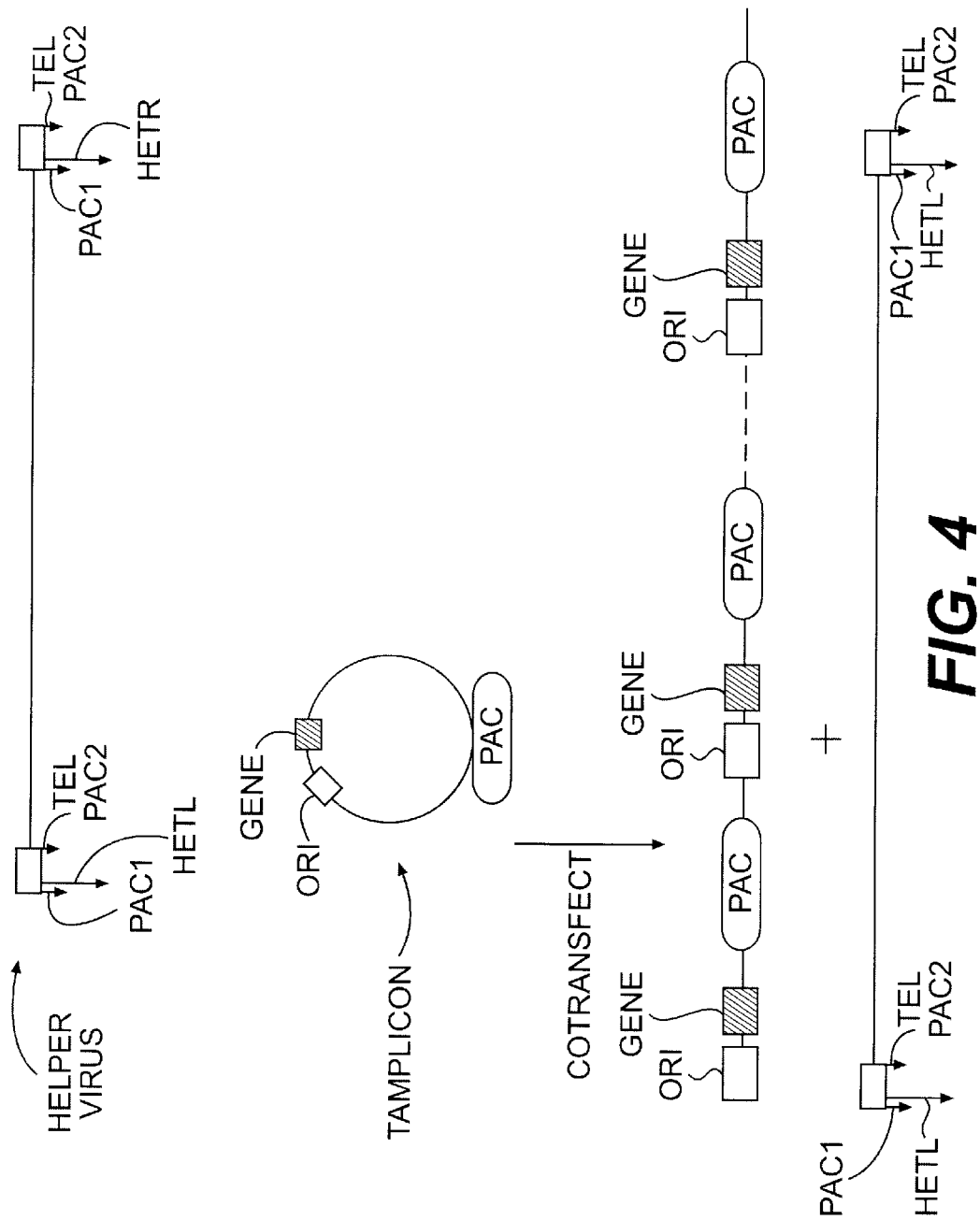
FIG. 4 is a schematic representation of a Tamplicon of the invention and the manner of its use together with a self-replicating virus.

Reference is now being made to FIG. 4 which is a schematic representation of the manner of use of a Tamplicon in combination with a helper virus. The Tamplicon comprises an origin of replication in combination with a pac site which comprises pac-1 and pac-2 sequences. When introduced into the cell a Tamplicon will not replicate in view of the fact that it lacks the transactivating factors encoded by the viral gene. Thus, in order to activate said gene, the Tamplicon is co-transfected with a helper virus. Following such co-transfection, the gene with its origin of replication becomes amplified in view of the formation of a concatemer and can then be expressed in large amounts. The presence of the pac sites ensures the cleavage into individual units, which can then either combine into the hosts' cells' genome or be packed in a viral particle encoded by the helper virus.

The use of the Tamplicon embodiment is at times advantageous seeing that it brings to the formation of many copies of said gene.

A preferred virus for use as a helper virus is the HHV-7, as already pointed out above, in view of its non-pathogenic nature. When the HHV-6 is used as the helper virus, means should be provided for its neutralization or destruction at some stage.

The invention will now be further illustrated in the following

EXAMPLES.

Example 1

HHV-7 is purified from infected cells, homogenized and centrifuged through dextran gradient. The resultant purified HHV-7 is cross-linked to magnetic beads and the beads carrying the HHV-7 are then incubated with each of the following cells:

(i) cells from a B cell line (e.g. Raji cells);

(ii) cells of the human cell line HeLa;

(iii) HeLa cells which were transfected with a CD4 gene and selected for expression of CD4; and (iv) HeLa sells which were transfected with a CD8 gene and selected for expression of CD8.

As a control, HHV-6 virions bound to magnetic beads (as described above) are incubated with the above cells.

After washing, CD4$^+$ cells, which are the HeLa cells transfected with the CD4 gene, remain bound to the magnetic beads by virtue of their binding to the HHV-7.

The binding of these cells to the HHV-7, can be inhibited by the use of anti-CD4 antibodies.

Example 2

HHV-7 virions are radioactively labelled by infecting cells with HHV-7 and labelling them with S35 methionine.

HHV-7 is extracted from the labelled cells, homogenized and centrifuged through dextran gradients. Magnetic beads are cross-linked with a CD4 protein or with soluble CD4 (sCD4) and the CD4-bound beads are incubated with the purified labelled HHV-7 virions.

Following incubation HHV-7 particles remain bound to the magnetic beads.

A non-ionic detergent NP40 is added to the beads-virion mixture to solubilize the envelope glycoproteins of the viruses. The beads are then washed and all virion proteins excluding the attached glycoprotein interacting with the CD4 receptor on the beads are washed away.

This glycoprotein is useful as a CD4-ligand of the invention.

Example 3

$CD4^+$ cells are purified from cord blood by methods known per se (Frenkel et al. 1990). The $CD4^+$ cells are activated for a day with phytohemaglutinin (PHA) and interluken-2 (IL2). Following activation, the $CD4^+$ cells are incubated for 20 minutes with anti-CD4 antibodies (e.g. anti-Leu3A) or with anti-CD8 antibodies (e.g. anti-Leu2A). Antibody concentrations have to be in the range of 0.01 $\mu$g/ml to 5.0 $\mu$g/ml. The $CD4^+$ cells are then incubated with HHV-7 or HHV-6 in the presence of the antibodies. Viral infection of the cells is monitored by methods known in the art, e.g. cytopathic effect (CPE) immunofluorescence assay (IFA), polymerase chain (PCR) or hybridization with various probes (such as pNF 2001 or pNF 1010).

Example 4

Children born to HIV positive mothers were analyzed for the following:

(i) HIV1 infection in serum (by PCR analysis);

(ii) HHV-7 infection in serum;

(iii) AIDS related symptoms.

Primary results of the above analysis are shown in the following Table 1.

TABLE 1

Seroconversion to HHV-7 in children born to HIV positive mothers

| Group | 9–12 months | 15–24 months |
|---|---|---|
| PCR– for HIV negative for AIDS related symptoms | 5/28 (18%) | 6/15 (40%) |
| PCR+ Asymptomatic | 4/10 (40%) | 4/9 (44.4%) |
| PCR+ positive for AIDS related symptoms | 4/9 (44.4%) | 2/9 (22.2%) |

As seen in the table, in the group of the 15–24 month old children infected with HIV a high percent of the children not showing AIDS related symptoms were also HHV-7 positive as compared to only a small percent of HHV-7 positive children in the group showing AIDS related symptoms. The percentage of the children carrying the HHV-7 virus in the HIV positive asymptomatic group was similar to the percentage of children carrying the HHV-7 in the group of children which were HIV negative and had no AIDS related symptoms. These results provide an indication that HHV-7 may have a possible effect on inhibiting progression of HIV infection.

Example 5

An autonomously replicating vector (ARV) was constructed as follows:

HHV-6 U1102 was cotransfected into Jurkat T cells together with a bacterial plasmid construct comprising the inserted gene and the neo selection gene both situated between two flanking heterogenous (het) sequences of HHV-6. The cotransfection was carried out by methods known in the art, e.g. electroporation. Inside the Jurkat cells recombination occurred at a high frequency between the het sequences of the bacterial plasmids and the HHV-6 resulting in the insertion of the gene and neo gene into the HHV-6 virus within its het region. The Jurkat T cells were further grown in a selection medium containing G418 enabling only cells comprising the recombinant HHV-6 virus containing the neo gene to grow. The recombinant viruses were then isolated from the cells, purified by terminal dilutions, tittered and analyzed by southern blot hybridization using methods known per se and suitable probes. As seen in FIG. 2, the resulting recombinant viruses (autonomously replicating vectors—ARV) comprised the gene of interest and the neo gene in their left and right heterogenous sequences.

It is to be noted that when using the HHV-6 U1102 other T cell lines may be used such as Jjhan or Molt 3 cells. When Z29-like viruses or HHV-7 are used (which do not efficiently replicate in continuous cell lines) PHA activated cord blood cells are typically used. It is also to be noted that the selection gene may be any one of several known selection genes (e.g. hygramycin or tynidine kinase (TK)). The cotransfection of the bacterial plasmid and the viral DNA may be carried out any one of several known methods, e.g. electroporation, the $CaCl_2$ method or DEAE dextran method, depending on the type of transfected cells used.

Example 6

A replication deficient vector (Tamplicon) was constructed by methods known in the art comprising a bacterial replication origin (ORI in FIG. 4), a drug selection gene, the cis acting sites of replication including the HHV-6 or HHV-7 replication origin, their cleavage packaging sequences (pac), additional genes with expression capabilities (e.g. a promoter and polyA signal) and a foreign nucleic acid sequence. The constructed Tamplicon was cotransfected into a T cell line (Jurkat, Molt 3 Jjahn or cord blood cells) together with either an HHV-6 or HHV-7 helper virus DNA. Alternatively, the constructed Tamplicon was first transfected into the T cells and only later the same cells were infected with HHV-6 or HHV-7 as the case may be. The transfection procedure as well as the later infection of the transfected cells was carried out according to any one of several known methods. Inside the transfected cells, transactivating factors encoded by the helper virus enable the replication of the Tamplicon from its origin resulting in a concatemer of the foreign nucleic acid sequence. The purification of the replicated Tamplicon from the cells was carried out by methods known per se.

Example 7

The pac2 sequence of the HHV-6 U1102 DNA was analyzed and the sequence is shown in FIG. 5A.

Example 8

The pac-2 sequence of the HHV-6 pNF1022 DNA was analyzed and the sequence is shown in FIG. 5B. As seen, the sequence is the junction between the TR and the unique sequence.

Example 9

The pac-1 sequence of HHV-6 pNF1022 was analyzed and the sequence is shown in FIG. 5C. The pac-1 signal away from the terminus was derived by fill in and flush ligation.

Example 10

The heterogenous sequence of one clone derived from the Z29 B substrain was subjected to several restriction enzymes and their sequence was analyzed by and is shown in FIG. 6.

Example 11

The HHV-6 pNF1022 DNA probe was subjected to restriction by the SaII restriction enzyme and the resulting 4 kb insert, spanning the junction of the left TR and the unique sequence, was sequenced. The full nucleic acid sequence of this fragment is shown in FIG. 7. The first and second origins of replication (ORF1 and ORF2) as well as the telomeric sequence (TEL) comprising 51 repeats of TAACCC and the pac-2 sequence which immediately follows the telomeric sequence and is further followed by the unique sequence are indicated in the figure.

Example 12

The pNF2009 (HA9) of HHV-7 DNA is a 2.1 kb insert resulting from restriction of the virus by the restriction enzyme HindIII and containing the two origins of replication. The nucleotide sequence of H49 is shown in FIG. 8.

Example 13

The Z29 strain of human herpesvirus-6 (HHV-6) (Lopez et al., 1988) was originally isolated from an AIDs patient in Zaire by Lopez et al. and was obtained from Carlos Lopez (Centers for Disease Control, Atlanta). The HHV-6 (Z29) was propagated in peripheral blood mononuclear cells (PBL) and in cord blood mononuclear cells (CBMC) (DiLuca et al., 1990 and Frankel et al. 1990, respectively). The cell extract containing the Z29 virus was purified by filtration and by terminal dilution resulting in pure cultures containing the A or B substrains of the virus. Each viral isolate was propagated for a number of times in two separate CBMC. The het sequence in each of the isolates propagated in each CBMC were compared and identical het sequences served as proof of the virus isolate originating from a certain patient.

The DNA replication of the infected cells was shut off after infection with the virus (DiLuca et al., 1990) and 32P-orthophosphate was added, enabling a significant fraction of 32P-orthophosphate to be preferentially incorporated into viral DNA. The 32P-labelled, virus infected, cell DNA was subjected to restriction by several restriction enzymes. Representative patterns of the resulting fragments are shown in FIG. 9.

Figure 9:
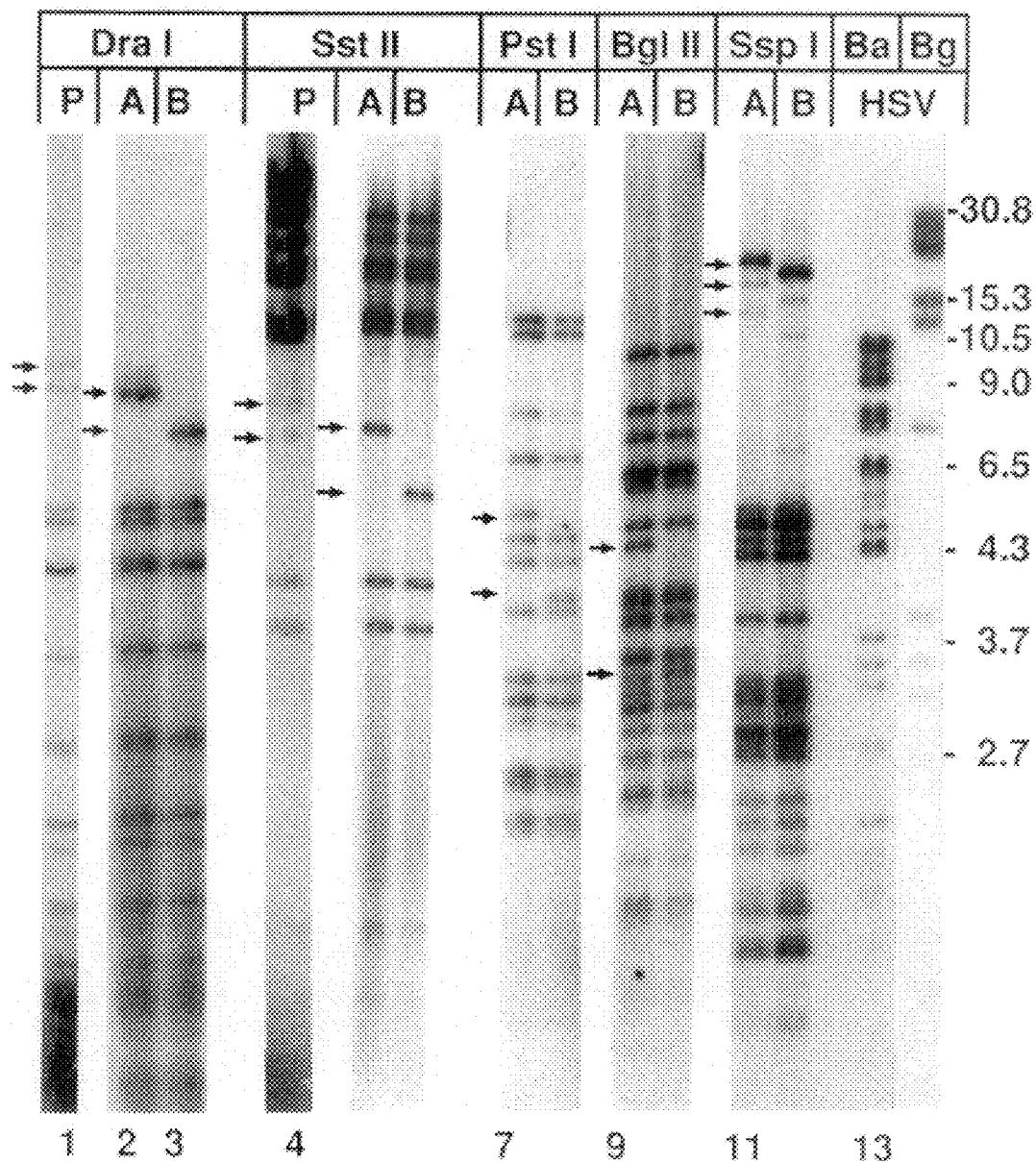
FIG. 9 shows an electrophoretogram of labelled DNAs from cells infected with the parent HHV-7 Z29, cleaved by a number of restriction enzymes. The DNA of HSV (herpes simplex virus) is shown for comparison.

As seen in FIG. 9, the parental (P in the figure) stock contains a mixture of two variants, A and B substrains which differ from one another by their restriction pattern.

Example 14

Figure 10:
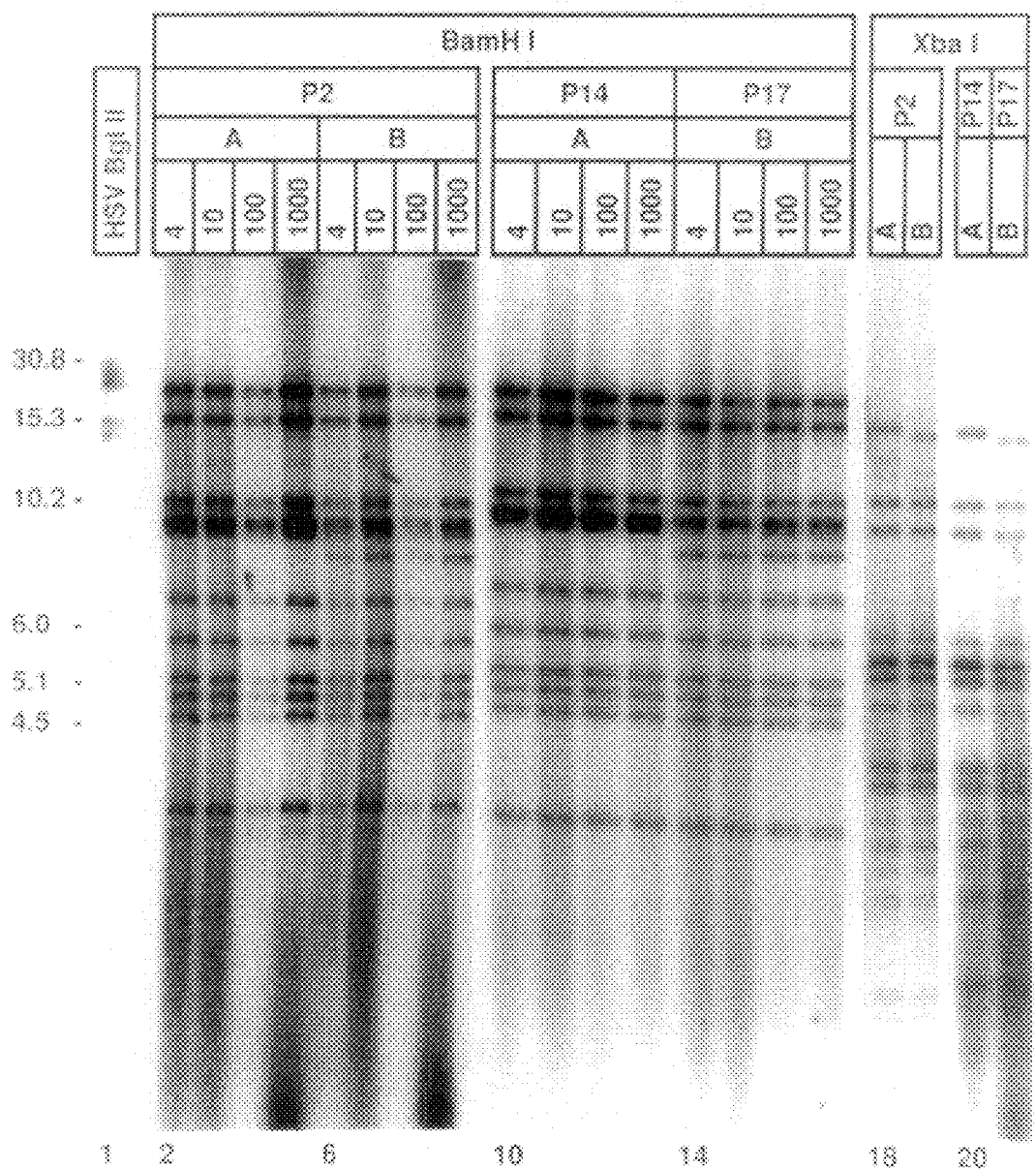
FIG. 10 shows an electrophoretogram of the DNA from the A and B substrains of HHV-6 Z29 strain, under different dilutions and following restriction by two restriction enzymes, after various passages in vitro.

The A and B substrains of the Z29 HHV-6 virus were propagated for 17 passages under different dilution modes (1:4, 1:10, 1:100, 1:1000). The various viruses were restricted by several endonuclease restriction enzymes. As seen in FIG. 10, the het BamH1 fragment in the A substrain is 10 kb long and the het BamH I fragment in the B substrain is 7.5 kb long. The het size remained stable from passage 2 through passage 17 in each one of the substrains.

These results show that the A and B substrains of Z29 are homogeneous and stable viruses, each comprising a different het fragment which remains stable throughout many passages.

Example 15

Figure 11:
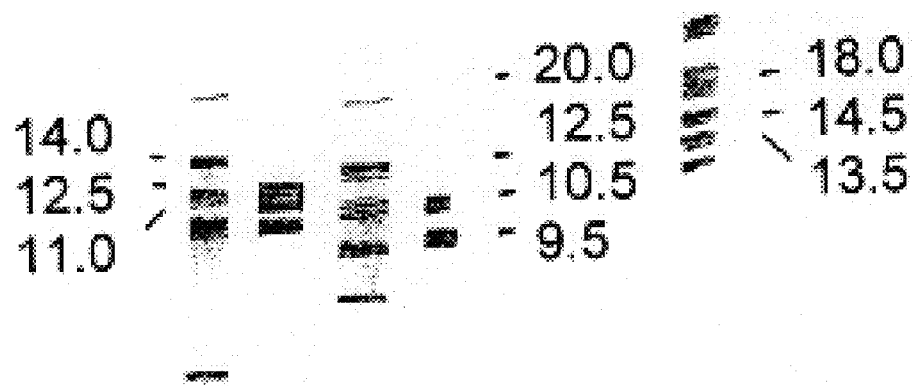
FIG. 11 shows an electrophoretogram of HHV-6 Z29 substrain A and B DNA isolated either from the nucleus (n) or from the cytoplasm (c)
Figure 12A:
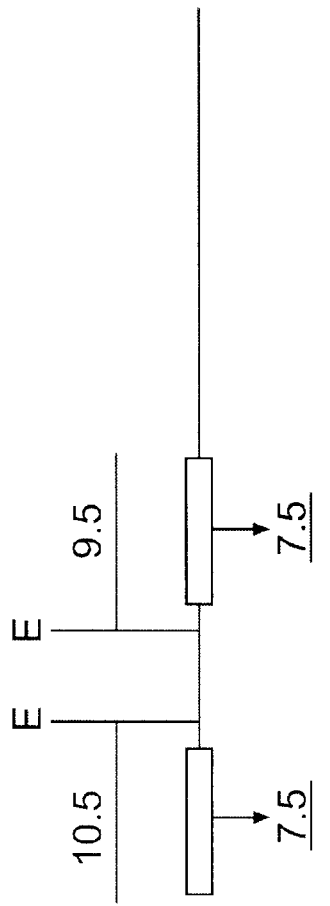
FIG. 12 is a schematic representation showing the size of the terminal fragments and the concatemeric junctions of the Z29 B substrain of HHV-6.
Figure 12B:
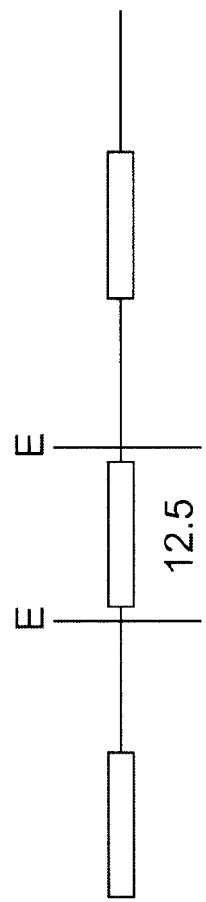
Figure 12C:
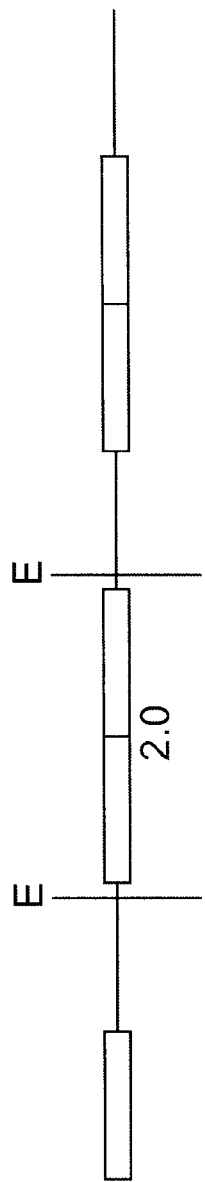
Figure 12D:
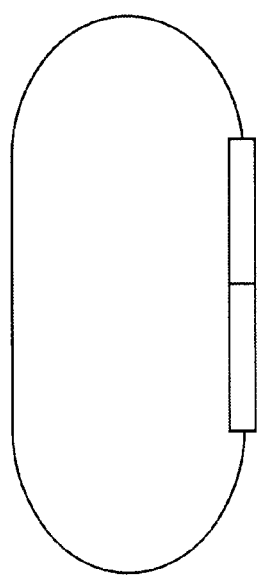

DNA was isolated from either the nucleus ("n" in FIG. 11) or the cytoplasm ("c" in FIG. 11) of cells infected with either Z29 A substrain or Z29 B substrain. The isolated DNA was cleaved with EcoRI, southern blotted and hybridized with a HHV-6 pNF1022 DNA probe (Frenkel et al. 1990, Schirmer et al., 1991). The pNF1022 probe is a 4 kb clone which contains the SaII L fragment of U1102 spanning the junction between the left terminal repeat (TRL) and the unique sequence two origin of replication and the telomeric sequence (see FIG. 9). This probe detects the concatemeric junctions and the terminal sequence of linear DNA.

As seen in the FIG., the nuclear DNA of cells infected both with the A substrain and the B substrain contained three fragments which hybridize with the HHV-6 U1102 probe. The three fragments represent linear packaged DNA having the length of a single unit, concatemeric nuclear DNA of which junctions comprise only a single terminal repeat (TR) and concatemeric nuclear DNA comprising two adjacent terminal repeat sequences. The concatemeric DNA comprising only a single TR most likely arose after recombination of the adjacent TRs (see FIG. 3). The concatemeric nuclear DNA comprising two adjacent TRs most likely arose as a result of rolling circle replication and is the species where cleavage is predicted to occur. The cytoplasmic DNA of cells infected with the A or B substrain contains two fragments which hybridize with the HHV-6 U1102 probe. These two fragments represent concatemeric nuclear DNA containing a single TR sequence and DNA containing two adjacent TRs. The species comprising two adjacent TRs (in which the EcoRI fragment is 20 kb long) is a minor component of the concatemeric DNA both in the nucleus and in the cytoplasm.

The length of the fragments terminal and the concatemeric junctions resulting from the EcoRI restriction enzyme in DNA isolated from cells infected with the A and B substrains is shown in Table 2 below.

TABLE 2

|  | Termainal fragments | | Concatemeric Junctions | |
| --- | --- | --- | --- | --- |
|  |  |  | TR | 2TR |
| EcoRI A | 11.0 | 12.5 | 14.0 | 23.5 |
| B | 9.5 | 10.5 | 12.5 | 20.0 |

A schematic representation of the concatemeric junctions of the HHV-6 Z29 B substrain is shown in FIG. 12.

What is claimed is:

1. A recombinant DNA molecule comprising:
   (a) a DNA sequence encoding HHV-6 or HHV-7, said DNA sequence encoding HHV-6 or HHV-7 comprising an origin of replication, a promoter sequence which induces expression in a T-cell host and a cleavage and packaging signal; and
   (b) a foreign nucleic acid sequence selected from the group consisting of a sequence coding for Thymidine Kinase, a sequence coding for glucocerebrosidase, a sequence coding for an insulin growth factor, a sequence coding for an insulin-like growth factor, a sequence coding for a protein which inhibits proliferation of malignant cells, a sequence coding for a protein which protects non-malignant cells from toxic effects of radiation, a sequence coding for a protein which protects non-malignant cell from toxic effects of chemotherapeutic agents, and combinations thereof.

2. A vector comprising the recombinant DNA molecule of claim 1.

3. The vector according to claim 2, wherein said vector is capable of autonomous replication.

4. A vector according to claim 2, wherein said vector is not capable of self replication and is used in combination with a helper virus.

5. The vector according to claim 2, wherein said vector is used for treatment of a T-cell related autoimmune disorder.

6. A recombinant DNA molecule comprising:
   (a) a DNA sequence encoding HHV-6 or HHV-7, said DNA sequence encoding HHV-6 or HHV-7 comprising an origin of replication, a promoter sequence which induces expression in a T-cell host and a cleavage and packaging signal; and
   (b) a foreign nucleic acid sequence, wherein said foreign nucleic acid sequence encodes a sequence which is an antisense sequence to an oncogene active in malignant lymphatic cells.

7. A vector comprising the recombinant DNA of molecule of claim 6.

* * * * *